United States Patent
Koehler et al.

(10) Patent No.: US 11,021,688 B2
(45) Date of Patent: Jun. 1, 2021

(54) DERIVATION OF HUMAN SKIN ORGANOIDS FROM PLURIPOTENT STEM CELLS

(71) Applicant: INDIANA UNIVERSITY RESEARCH AND TECHNOLOGY CORPORATION, Indianapolis, IN (US)

(72) Inventors: Karl R. Koehler, Indianapolis, IN (US); Jiyoon Lee, Indianapolis, IN (US)

(73) Assignee: INDIANA UNIVERSITY RESEARCH ANND TECHNOLOGY CORPORATION, Indianapolis, IN (US)

( * ) Notice: Subject to any disclaimer, the term of this patent is extended or adjusted under 35 U.S.C. 154(b) by 110 days.

(21) Appl. No.: 15/769,139

(22) PCT Filed: Oct. 21, 2016

(86) PCT No.: PCT/US2016/058174
§ 371 (c)(1),
(2) Date: Apr. 18, 2018

(87) PCT Pub. No.: WO2017/070506
PCT Pub. Date: Apr. 27, 2017

(65) Prior Publication Data
US 2018/0305671 A1   Oct. 25, 2018

Related U.S. Application Data

(60) Provisional application No. 62/244,612, filed on Oct. 21, 2015.

(51) Int. Cl.
*C12N 5/071* (2010.01)
*A61L 27/60* (2006.01)
(Continued)

(52) U.S. Cl.
CPC ............ *C12N 5/0698* (2013.01); *A61K 35/36* (2013.01); *A61L 27/362* (2013.01); *A61L 27/3633* (2013.01); *A61L 27/3641* (2013.01); *A61L 27/3687* (2013.01); *A61L 27/3813* (2013.01); *A61L 27/3834* (2013.01); *A61L 27/3839* (2013.01); *A61L 27/3891* (2013.01); *A61L 27/3895* (2013.01); *A61L 27/52* (2013.01); *A61L 27/54* (2013.01); *A61L 27/56* (2013.01); *A61L 27/58* (2013.01); *A61L 27/60* (2013.01); *C12N 5/0627* (2013.01); *C12N 5/0629* (2013.01); *C12N 5/0656* (2013.01); *C12Q 1/6876* (2013.01); *A61L 2300/412* (2013.01); *A61L 2300/604* (2013.01); *A61L 2300/64* (2013.01); *A61L 2430/34* (2013.01); *A61L 2430/40* (2013.01); *C12N 2501/115* (2013.01); *C12N 2501/15* (2013.01); *C12N 2501/155* (2013.01); *C12N 2501/999* (2013.01); *C12N 2502/092* (2013.01); *C12N 2502/094* (2013.01); *C12N 2502/1323* (2013.01); *C12N 2506/02* (2013.01); *C12N 2506/03* (2013.01); *C12N 2506/1346* (2013.01); *C12N 2506/45* (2013.01); *C12N 2513/00* (2013.01);
(Continued)

(58) Field of Classification Search
CPC .. C12N 5/0698; C12N 5/0627; C12N 5/0629; C12N 5/0656; C12N 2501/115; C12N 2501/15; C12N 2501/155; C12N 2501/999; C12N 2502/092; C12N 2502/094; C12N 2502/1323; C12N 2506/02; C12N 2506/03; C12N 2506/1346; C12N 2506/45; C12N 2513/00; C12N 2533/76; C12N 2533/90; A61K 35/36; A61L 27/362; A61L 27/3633; A61L 27/3641; A61L 27/3687; A61L 27/3813; A61L 27/3834; A61L 27/3839; A61L 27/3891; A61L 27/3895; A61L 27/52; A61L 27/54; A61L 27/56; A61L 27/58; A61L 27/60; A61L 2300/412; A61L 2300/604; A61L 2300/64; A61L 2430/34; A61L 2430/40; C12Q 1/6876; C12Q 2600/136
See application file for complete search history.

(56) References Cited

U.S. PATENT DOCUMENTS

2008/0139469 A1   6/2008   Imamura et al.
2008/0171385 A1   7/2008   Bergendahl
(Continued)

FOREIGN PATENT DOCUMENTS

| JP | 2006-083082 A | 3/2006 |
| WO | 2003051419 A1 | 6/2003 |
| WO | WO 2013166488 A1 | 11/2013 |

OTHER PUBLICATIONS

Leung et al. (Dev Biol. Jul. 15, 2013; 379(2): 208-220).*
(Continued)

*Primary Examiner* — Thaian N. Ton
(74) *Attorney, Agent, or Firm* — Quarles & Brady LLP

(57) ABSTRACT

Provided herein are methods for directing differentiation of human pluripotent stem cells into a three-dimensional multilayered skin composition comprising an epidermal layer, a dermal layer, and a plurality of cells capable of forming a functional hair follicle. Also provided herein are three-dimensional, multilayered engineered skin compositions and methods of using the same for drug screening, for screening compounds for effects on hair growth, and for other applications.

15 Claims, 21 Drawing Sheets

(51) Int. Cl.
| | |
|---|---|
| A61L 27/38 | (2006.01) |
| A61K 35/36 | (2015.01) |
| C12N 5/077 | (2010.01) |
| A61L 27/36 | (2006.01) |
| A61L 27/52 | (2006.01) |
| A61L 27/54 | (2006.01) |
| A61L 27/56 | (2006.01) |
| A61L 27/58 | (2006.01) |
| C12Q 1/6876 | (2018.01) |

(52) U.S. Cl.
CPC ...... *C12N 2533/76* (2013.01); *C12N 2533/90* (2013.01); *C12Q 2600/136* (2013.01)

(56) References Cited

U.S. PATENT DOCUMENTS

| | | |
|---|---|---|
| 2011/0321180 A1 | 12/2011 | Lee et al. |
| 2012/0148541 A1 | 6/2012 | Lee et al. |
| 2016/0213717 A1 | 7/2016 | Xu |

OTHER PUBLICATIONS

Zhang et al. Development. Jul. 2010;137(13):2095-105.*
Harvey et al. J Cell Sci. May 15, 2010; 123(Pt 10): 1796-804.*
Medvinsky, A. et al. On human development: lessons from stem cell systems. Development 142, 17-20 (2015).
Merkle, F. T. et al. Efficient CRISPR-Cas9-Mediated Generation of Knockin Human Pluripotent Stem Cells Lacking Undesired Mutations at the Targeted Locus. Cell Rep 11, 875-883 (2015).
Metallo, C. M., et al. Retinoic acid and bone morphogenetic protein signaling synergize to efficiently direct epithelial differentiation of human embryonic stem cells. Stem Cells 26, 372-380 (2008).
Mica, Y., et al. Modeling neural crest induction, melanocyte specification, and disease-related pigmentation defects in hESCs and patient-specific iPSCs. Cell Rep 3, 1140-1152 (2013).
Mort, R. L., et al. Ex vivo culture of mouse embryonic skin and live-imaging of melanoblast migration. J Vis Exp (2014). doi:10.3791/51352.
Moscona, A. et al. The dissociation and aggregation of cells from organ rudiments of the early chick embryo. Journal of Anatomy 86, 287-301 (1952).
Moscona, A. Rotation-mediated histogenetic aggregation of dissociated cells. A quantifiable approach to cell interactions in vitro. Experimental cell research 22, 455-475 (1961).
Nakano, T. et al. Self-Formation of Optic Cups and Storable Stratified Neural Retina from Human ESCs. Cell Stem cell 10, 771-785 (2012).
Narisawa, Y., et al. (1994). Merkel Cells of the Terminal Hair Follicle of the Adult Human Scalp. Journal of Investigative Dermatology, 102(4), 506-510.
Oh, J. W. et al. A Guide to Studying Human Hair Follicle Cycling In Vivo. The Journal of investigative dermatology 136, 34-44 (2016).
Oh, J. W., et al. Organotypic skin culture. The Journal of investigative dermatology 133, e14 (2013).
Paladini, R. D., et al. Modulation of hair growth with small molecule agonists of the hedgehog signaling pathway. Journal of Investigative Dermatology 125, 638-646 (2005).
Paus, R. et al. A comprehensive guide for the recognition and classification of distinct stages of hair follicle morphogenesis. The Journal of investigative dermatology 113, 523-532 (1999).
Philpott, M. P. et al. Effects of EGF on the morphology and patterns of DNA synthesis in isolated human hair follicles. Journal of Investigative Dermatology 102, 186-191 (1994).
Philpott, M. P., et al. Human hair growth in vitro. Journal of cell science 97 ( Pt 3), 463-471 (1990).
Prasain, N., et al. "Differentiation of human pluripotent stem cells to cells similar to cord-blood endothelial colony-forming cells." Nature biotechnology 32.11 (2014): 1151.

Ramot, Y. et al. Advanced inhibition of undesired human hair growth by PPAR? modulation? The Journal of Investigative dermatology 134, 1128-1131 (2014).
Ranga, A., et al. Drug discovery through stem cell-based organoid models. Adv. Drug Deliv. Rev. 69-70, 19-28 (2014).
Sandoe, J. et al. Opportunities and challenges of pluripotent stem cell neurodegenerative disease models. Nature Neuroscience 16, 780-789 (2013).
Schlaeger, T M. et al. A comparison of non-integrating reprogramming methods. Nature Biotechnology (2014). doi:10.1038/nbt.3070.
Schneider, M. R., et al. The hair follicle as a dynamic miniorgan. Current biology: CB 19, R132-42 (2009).
Sebastiano, V. et al. Human COL7A1-corrected induced pluripotent stem cells for the treatment of recessive dystrophic epidermolysis bullosa. Science translational medicine 6, 264ra163-264ra163 (2014).
Soma, T., et al. Hair-inducing ability of human dermal papilla cells cultured under Wnt/β-catenin signalling activation. Experimental Dermatology 21, 307-309 (2012).
Soma, T., et al. Involvement of transforming growth factor-beta2 in catagen induction during the human hair cycle. Journal of Investigative Dermatology 118, 993-997 (2002).
Stenn, K. S. et al. Controls of hair follicle cycling. Physiological reviews 81, 449-494 (2001).
St-Jacques, B. et al. Sonic hedgehog signaling is essential for hair development. Current biology : CB 8, 1058-1068 (1998).
Sun, B. K., et al. Advances in skin grafting and treatment of cutaneous wounds. Science 346, 941-945 (2014).
Takagi, R. et al. Bioengineering a 3D integumentary organ system from iPS cells using an in vivo transplantation model. Science Advances 2, e1500887-e1500887 (2016).
Takasato, M. et al. Kidney organoids from human iPS cells contain multiple lineages and model human nephrogenesis. Nature 526, 564-568 (2015).
Thomson, J. A., et al. "Embryonic stem cell lines derived from human blastocysts." science 282.5391 (1998): 1145-1147.
Tsuji, Y. et al. A potential suppressor of TGF-beta delays catagen progression in hair follicles. J. Investig. Dermatol. Symp. Proc. 8, 65-68 (2003).
Umegaki-Arao, N. et al. Induced pluripotent stem cells from human revertant keratinocytes for the treatment of epidermolysis bullosa. Science translational medicine 6, 264ra164 (2014).
Volkner, M. et al. Retinal Organoids from Pluripotent Stem Cells Efficiently Recapitulate Retinogenesis. Stem Cell Reports 6, 525-538 (2016).
Watanabe K, et al., "A ROCK inhibitor permits survival of dissociated human embryonic stem cells," Nat. Biotechnol. 25:681-686 (2007).
Watt, F. M. Mammalian skin cell biology: at the interface between laboratory and clinic. Science 346, 937-940 (2014).
Wenzel, D. et al. Genetically corrected iPSCs as cell therapy for recessive dystrophic epidermolysis bullosa. Science translational medicine 6, 264ra165 (2014).
Wright, M. C., et al. (2015). Unipotent, Atoh1+ progenitors maintain the Merkel cell population in embryonic and adult mice. The Journal of Cell Biology, 208(3), 367-379.
Wu, X., et al. Full-thickness skin with mature hair follicles generated from tissue culture expanded human cells. Tissue Eng Part A 20, 3314-3321 (2014).
Xing, L. et al. Alopecia areata is driven by cytotoxic T lymphocytes and is reversed by JAK inhibition. Nature medicine 20, 1043-1049 (2014).
Yamanaka, S. Induced Pluripotent Stem Cells: Past, Present, and Future. Cell Stem Cell 10, 678-684 (2012).
Yang, R. et al. Generation of folliculogenic human epithelial stem cells from induced pluripotent stem cells : Nature Communications : Nature Publishing Group. Nature Communications 5, 3071 (2014).
Yannas, I. V. et al. Design of an artificial skin. I. Basic design principles. J. Biomed. Mater. Res. 14, 65-81 (1980).
Yu, J., et al. "Human induced pluripotent stem cells free of vector and transgene sequences." Science 324.5928 ,2009):797-801.
Yu, J., et al. "Induced pluripotent stem cell lines derived from human somatic cells." science 318.5858 (2007): 1917-1920.

(56) References Cited

OTHER PUBLICATIONS

International Search Report and Written Opinion for international application No. PCT/US2016/058174 dated Jan. 17, 2017, 13 pages.
Guo et al., Building a Microphysiological Skin Model from Induced Pluripotent Stem Cells, Stem Cell Research and Therapy, Dec. 20, 2013, pp. 1-7, 7 pages.
Brohem et al., Artificial Skin in Perspective: Concepts and Applications, Feb. 2011, vol. 24 No. 1, pp. 1-25, 25 pages.
Chittur et al., Inhibition of Inflammatory Gene Expression in Keratinocytes Using a Composition Containing Carnitine, Thioctic Acid and Saw Plametto Extract, Evidence Based Complementary Alternative Medicine, Jun. 8, 2011, 7 pages.
Beers, J. et al. Passaging and colony expansion of human pluripotent stem cells by enzyme-free dissociation in chemically defined culture conditions. Nature Protocols 7, 2029-2040 (2012).
Bell, E., et al. Living tissue formed in vitro and accepted as skin-equivalent tissue of full thickness. Science 211, 1052-1054 (1981).
Blanpain, C. et al. Stem cell plasticity. Plasticity of epithelial stem cells in tissue regeneration. Science 344, 1242281-1242281 (2014).
Bodó, E. et al. Dissecting the impact of chemotherapy on the human hair follicle: a pragmatic in vitro assay for studying the pathogenesis and potential management of hair follicle dystrophy. The American journal of pathology 171, 1153-1167 (2007).
Chapman, S., et al. Human keratinocytes are efficiently immortalized by a Rho kinase inhibitor. The Journal of clinical investigation 120, 2619-2626 (2010).
Chen, G. et al. Chemically defined conditions for human iPSC derivation and culture. Nature Methods 8, 424-429 (2011).
Chuong, C.-M., et al. Defining hair follicles in the age of stem cell bioengineering. The Journal of investigative dermatology 127, 2098-2100 (2007).
Colombe, L., et al. Prostaglandin metabolism in human hair follicle. Experimental Dermatology 16, 762-769 (2007).
Coraux, C. et al. Reconstituted skin from murine embryonic stem cells. Current biology : CB 13, 849-853 (2003).
Driskell, R. R. et al. Distinct fibroblast lineages determine dermal architecture in skin development and repair. Nature 504, 277-281 (2013).
Driskell, R. R. et al. Understanding fibroblast heterogeneity in the skin. Trends in cell biology (2014). doi:10.1016/j.tcb.2014.10.001.
Zheng, Y. et al. Mature hair follicles generated from dissociated cells: a universal mechanism of folliculoneogenesis. Developmental dynamics : an official publication of the American Association of Anatomists 239, 2619-2626 (2010).
Driskell, R. R., et al. Defining dermal adipose tissue. Experimental Dermatology 23, 629-631 (2014).
Ebert, A. D., et al. "Induced pluripotent stem cells from a spinal muscular atrophy patient." Nature 457.7227 (2009): 277.
European Patent Office, European Search Report for application 16858318, dated Feb. 25, 2019, 12 pages.
Gilhar, A., et al. Alopecia areata. N. Engl. J. Med. 366, 1515-1525 (2012).
Gledhill, K., et al. "Melanin transfer in human 3D skin equivalents generated exclusively from induced pluripotent stem cells." PloS one 10.8 (2015): e0136713.
Gnedeva, K. et al. Derivation of hair-inducing cell from human pluripotent stem cells. PLoS ONE 10, e0116892 (2015).
Green, H., et al. Marker succession during the development of keratinocytes from cultured human embryonic stem cells. Proceedings of the National Academy of Sciences of the United States of America 100, 15625-15630 (2003).
Guenou, H. et al. Human embryonic stem-cell derivatives for full reconstruction of the pluristratified epidermis: a preclinical study. Lancet 374, 1745-1753 (2009).
Hanna, J. H., et al. Pluripotency and cellular reprogramming: facts, hypotheses, unresolved issues. Cell 143, 508-525 (2010).
Hardy, M. H. The development of mouse hair in vitro with some observations on pigmentation. Journal of Anatomy 83, 364-84—3 pl (1949).

Harel, S. et al. Pharmacologic inhibition of JAK-STAT signaling promotes hair growth. Science Advances 1, e1500973-e1500973 (2015).
Hiler, D. et al. Quantification of Retinogenesis in 3D Cultures Reveals Epigenetic Memory and Higher Efficiency in PSCs Derived from Rod Photoreceptors. Cell Stem Cell 17, 101-115 (2015).
Hockemeyer, D. et al. Genetic engineering of human pluripotent cells using TALE nucleases. Nature Biotechnology (2011). doi:10.1038/nbt.1927.
Howden, S. E., et al. "Genetic correction and analysis of induced pluripotent stem cells from a patient with gyrate atrophy." Proceedings of the National Academy of Sciences 108.16 (2011): 6537-6542.
Hsu, Y.-C., et al. Emerging interactions between skin stem cells and their niches. Nature medicine 20, 847-856 (2014).
Huch, M. et al. Modeling mouse and human development using organoid cultures. Development 142, 3113-3125 (2015).
Ito, T. et al. Interferon-gamma is a potent inducer of catagen-like changes in cultured human anagen hair follicles. Br. J. Dermatol. 152, 623-631 (2005).
Itoh, M. et al. Generation of 3D skin equivalents fully reconstituted from human induced pluripotent stem cells (iPSCs). PLoS ONE 8, e77673 (2013).
Itoh, M., et al. Generation of keratinocytes from normal and recessive dystrophic epidermolysis bullosa-induced pluripotent stem cells. PNAS 108, 8797-8802 (2011).
Jindo, T. et al. The effect of hepatocyte growth factor/scatter factor on human hair follicle growth. Journal of Dermatological Science 10, 229-232 (1995).
Kandárová, H., et al. An In Vitro Skin Irritation Test (SIT) using the EpiDerm Reconstructed Human Epidermal (RHE) Model. J Vis Exp e1366—e1366 (2009). doi:10.3791/1366.
Kloepper, J. E. et al. Methods in hair research: how to objectively distinguish between anagen and catagen in human hair follicle organ culture. Experimental Dermatology 19, 305-312 (2010).
Koehler, K. R. et al. 3D mouse embryonic stem cell culture for generating inner ear organoids. Nature Protocols 9, 1229-1244 (2014).
Koehler, K. R., et al. (2013). Generation of inner ear sensory epithelia from pluripotent stem cells in 3D culture. Nature, 500(7461), 217-221.
Kwack, M. H., et al. Dihydrotestosterone-inducible IL-6 inhibits elongation of human hair shafts by suppressing matrix cell proliferation and promotes regression of hair follicles in mice. The Journal of investigative dermatology 132, 43-49 (2012).
Lancaster, M. A. et al. Organogenesis in a dish: modeling development and disease using organoid technologies. Science 345, 1247125 (2014).
Langan, E. A., et al. Human hair follicle organ culture: theory, application and perspectives. Experimental Dermatology 24, 903-911 (2015).
Lee, J., et al. "Hair follicle development in mouse pluripotent stem cell-derived skin organoids." Cell reports 22.1 (2018): 242-254.
Lee, L. F., et al. A simplified procedure to reconstitute hair-producing skin. Tissue Eng Part C Methods 17, 391-400 (2011).
Lee, Y. R., et al. Hepatocyte growth factor (HGF) activator expressed in hair follicles is involved in in vitro HGF-dependent hair follicle elongation. Journal of Dermatological Science 25, 156-163 (2001).
Lesko, M. H., et al. Sox2 modulates the function of two distinct cell lineages in mouse skin. Developmental biology (2013). doi:10.1016/j.ydbio.2013.08.004.
Li, L., et al. The Three-Dimensional Human Skin Reconstruct Model: a Tool to Study Normal Skin and Melanoma Progression. J Vis Exp e2937-e2937 (2011). doi:10.3791/2937.
Liakath-Ali, K. et al. Novel skin phenotypes revealed by a genome-wide mouse reverse genetic screen. Nature Communications 5, 3540 (2014).
Liu, X.-P., et al. Functional development of mechanosensitive hair cells in stem cell-derived organoids parallels native vestibular hair cells. Nature Communications 7, 11508 (2016).
Lu, B., et al. "Long-term safety and function of RPE from human embryonic stem cells in preclinical models of macular degeneration." Stem cells 27.9 (2009): 2126-2135.

(56) References Cited

OTHER PUBLICATIONS

Lu, C. et al. Sweat gland progenitors in development, homeostasis, and wound repair. Cold Spring Harb Perspect Med 4, a015222 (2014).

Ludwig T, et al., "Derivation of human embryonic stem cells in defined conditions," Nat. Biotechnol. 24:185-187 (2006).

Ludwig T, et al., "Feeder-independent culture of human embryonic stem cells," Nat. Methods 3:637-646 (2006).

Office action issued for JP 2018-520393 dated Nov. 10, 2020.

* cited by examiner

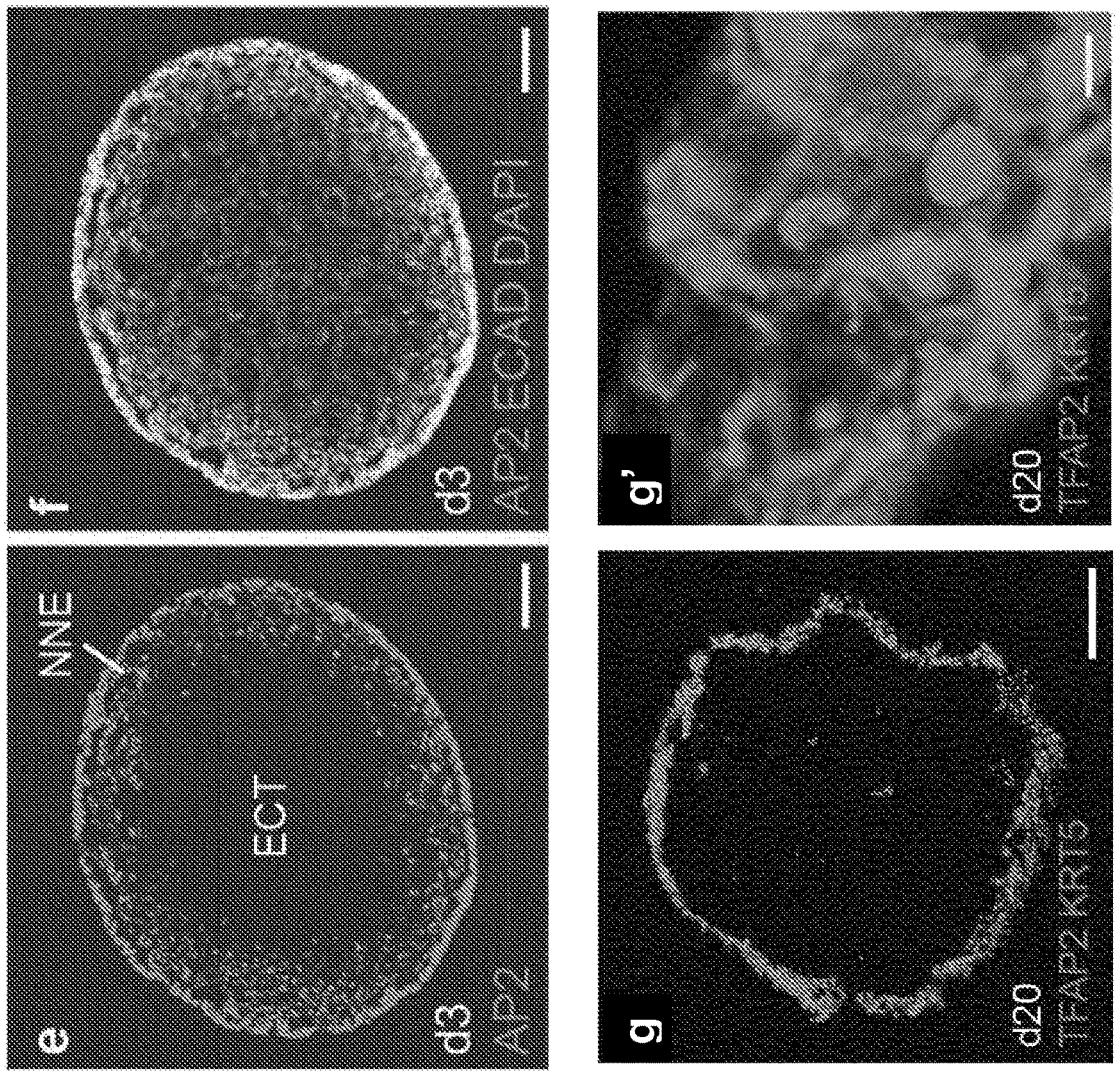
FIGS. 3A-3G, CONTINUED

FIGS. 12A-12H
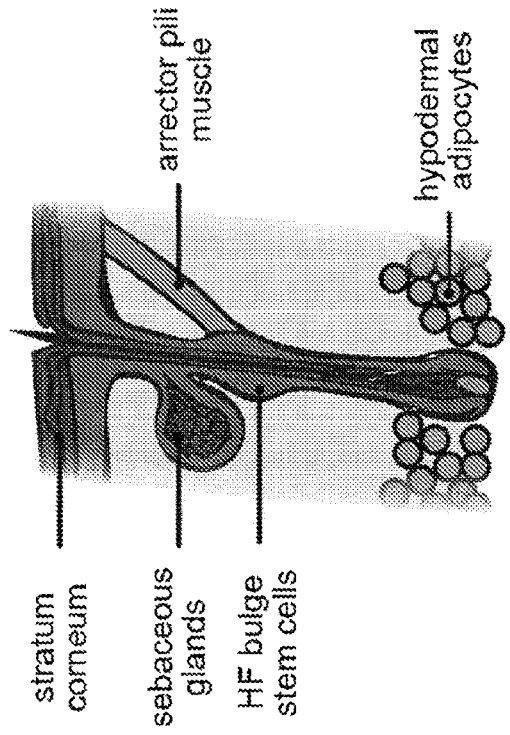
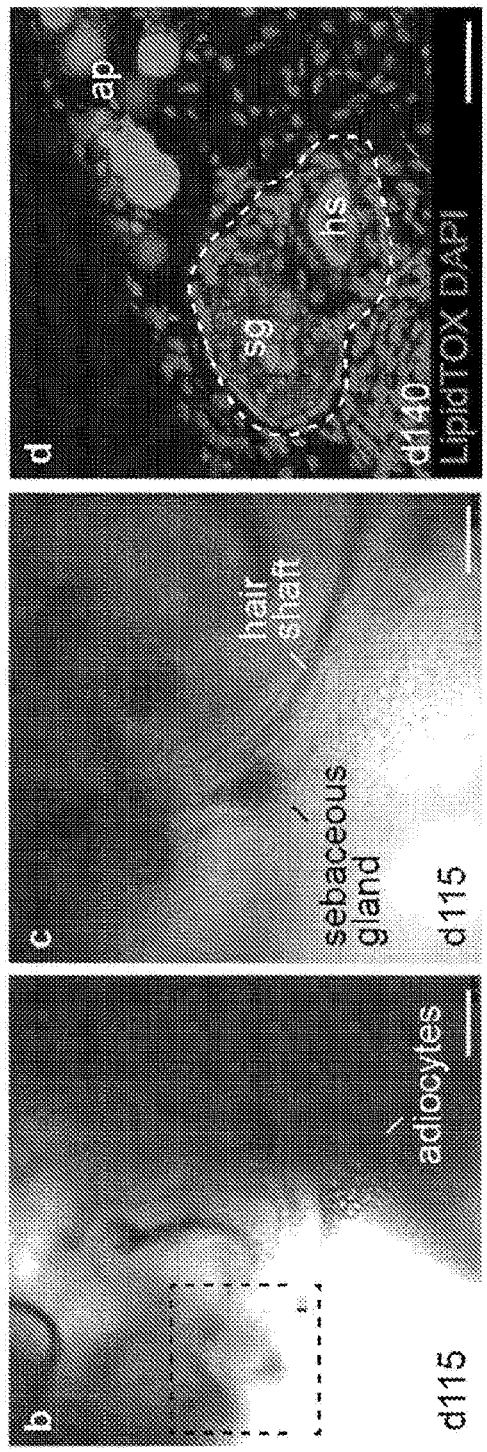

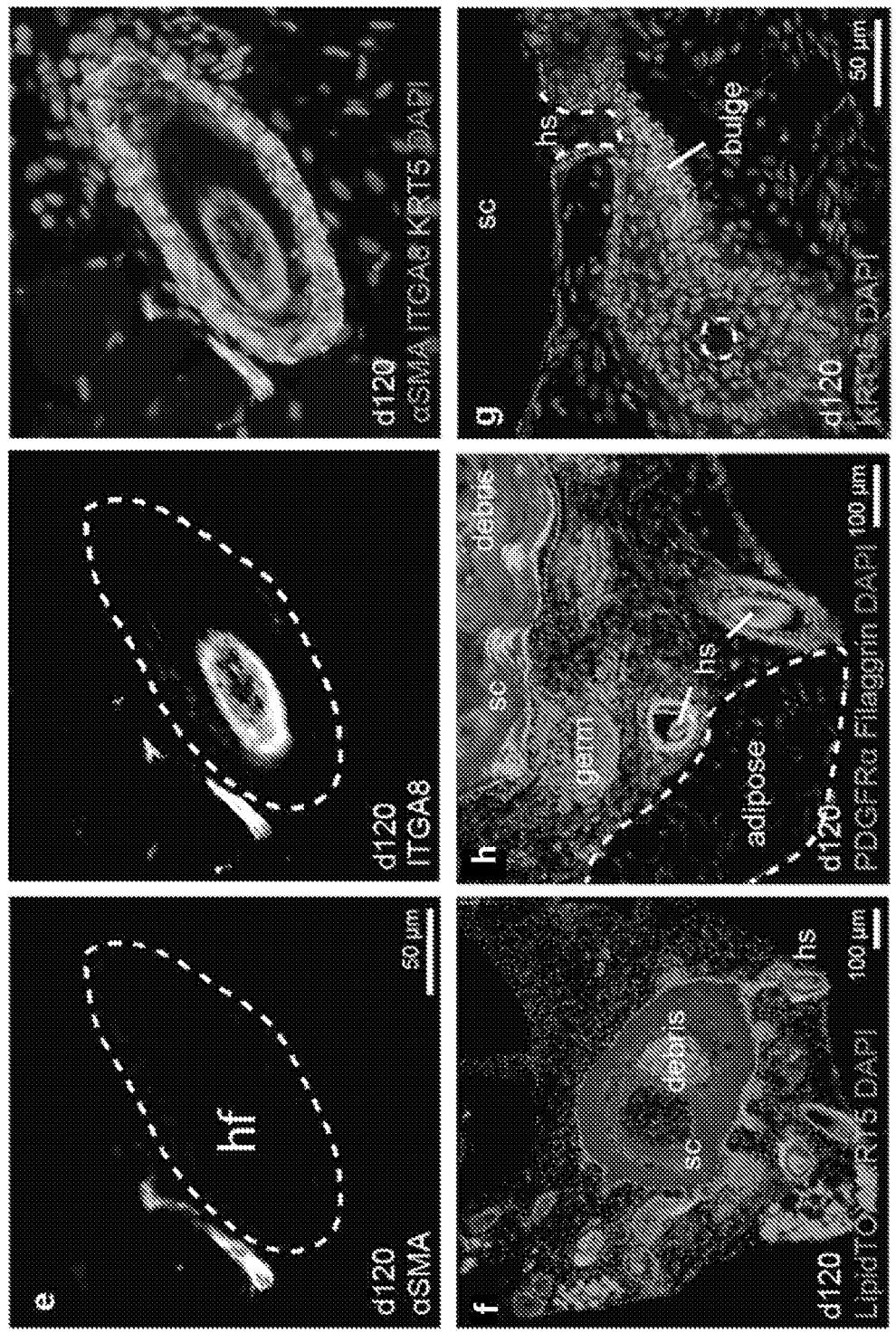
FIGS. 12A-12H, CONTINUED

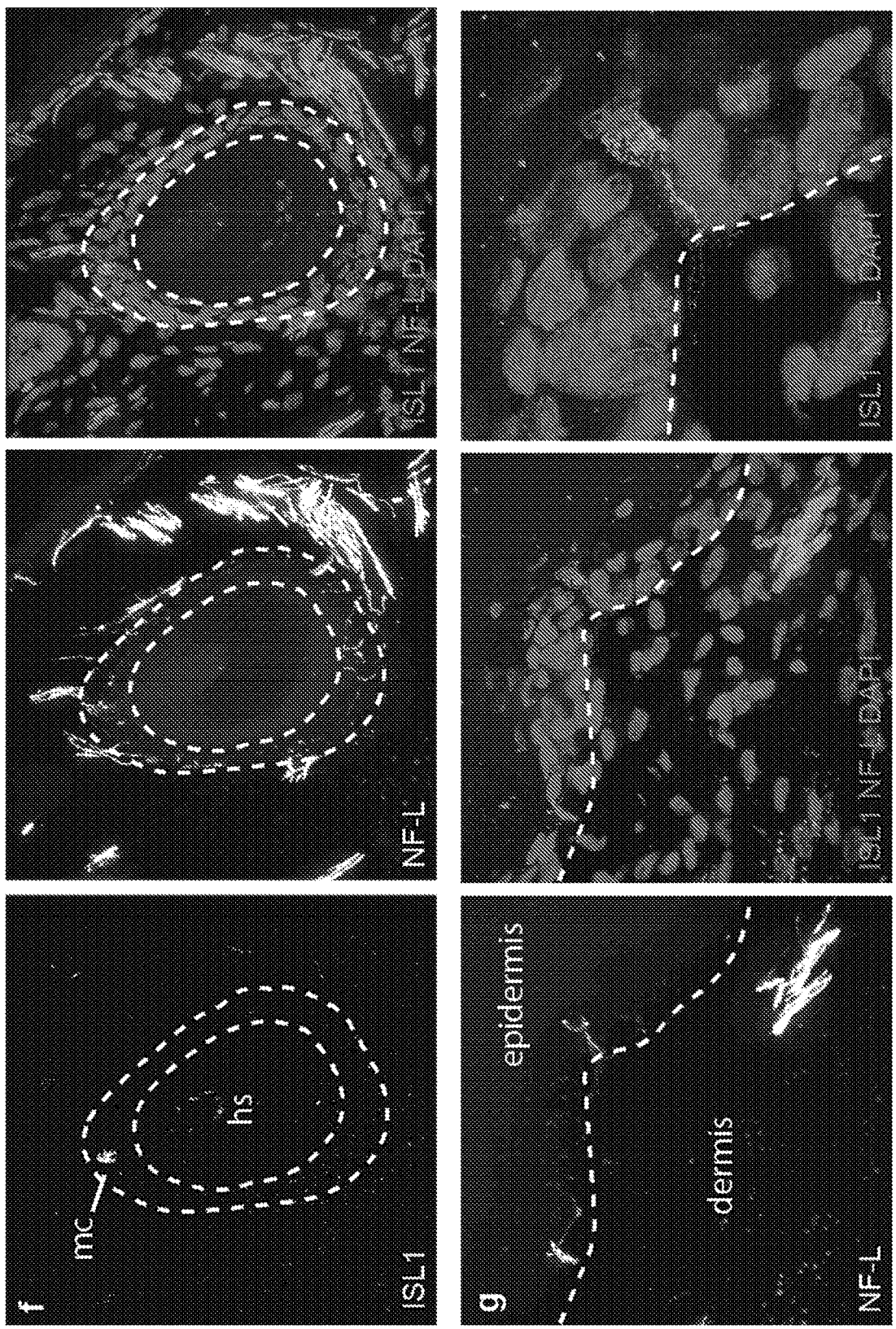

FIGS. 15A-15B, CONTINUED
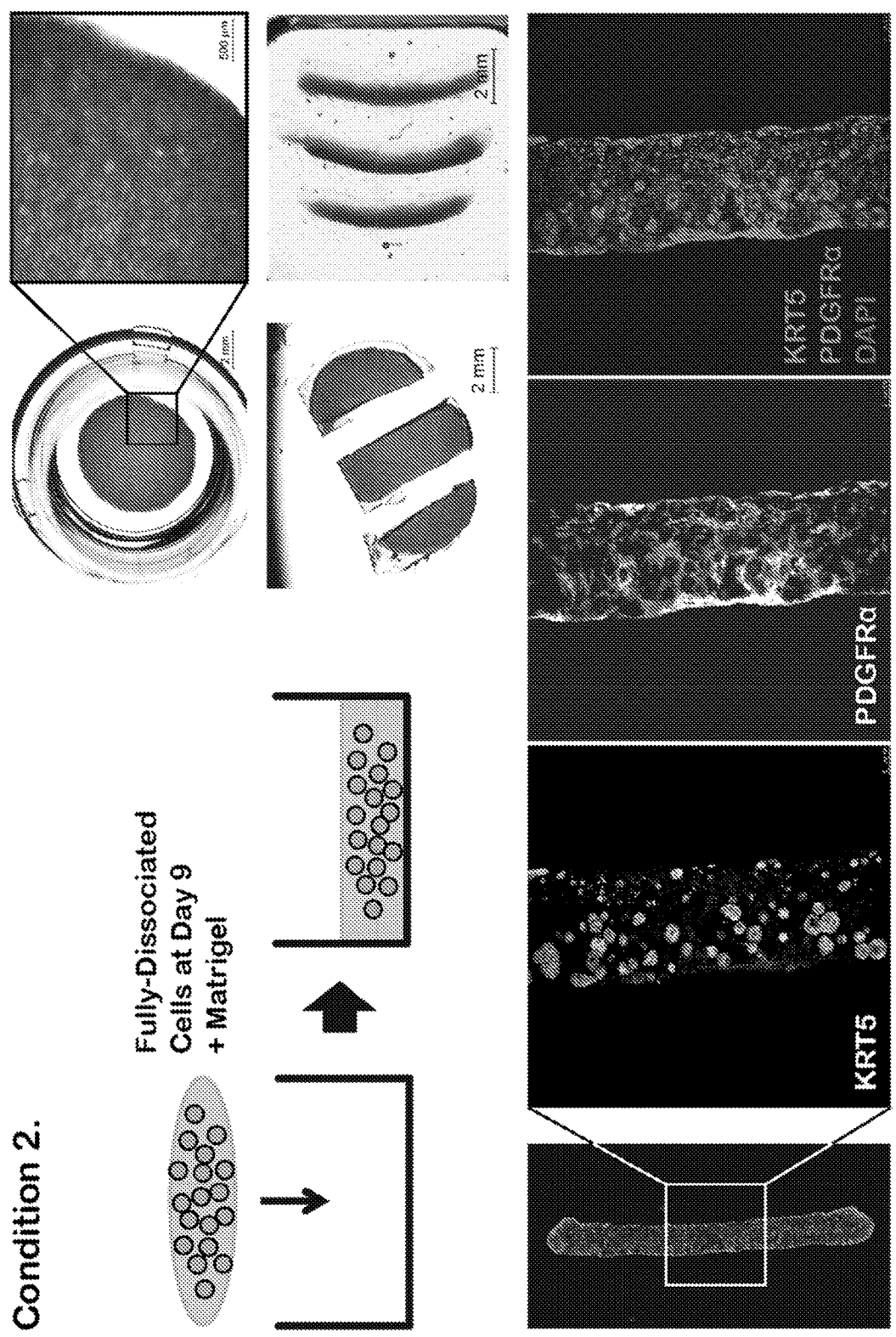

DERIVATION OF HUMAN SKIN ORGANOIDS FROM PLURIPOTENT STEM CELLS

CROSS-REFERENCE TO RELATED APPLICATIONS

This application represents the U.S. National Stage of International Application No. PCT/US2016/058174, filed Oct. 21, 2016, which claims the benefit of U.S. Provisional Application No. 62/244,612, filed Oct. 21, 2015, which is incorporated herein by reference as if set forth in its entirety.

STATEMENT REGARDING FEDERALLY SPONSORED RESEARCH OR DEVELOPMENT

This invention was made with government support under DC013294 and DC015624 awarded by the National Institutes of Health. The government has certain rights in the invention.

FIELD OF THE INVENTION

Provided herein are methods for directing differentiation of human pluripotent stem cells into human skin organoids comprising hair shafts. More particularly, provided herein are methods for obtaining three-dimensional cultures comprising human pluripotent stem cell-derived epidermis and dermis layers that contain functional hair follicles.

BACKGROUND OF THE INVENTION

The skin is the primary barrier between the body and the outside world: it regulates temperature and water retention, guards against infection and foreign body intrusion, and mediates touch and pain sensation. As the first line of defense, the skin is susceptible to temperature or radiation extremes that can cause burns as well as cancers and genetic defects. Burns affect over 11 million people worldwide annually. In the United States, approximately 70 million surgical procedures are performed each year; with one-third of these procedures resulting in scarring. From a clinical standpoint, skin of the head and neck is particularly vulnerable and difficult to reconstruct after a major injury. Today, if a large patch of skin needs to be replaced, the typical course of action is to transplant skin from other parts of the body or use artificial skin substitutes to close the wound. However, the availability of sufficient tissues for autologous grafting and the inability of skin substitutes to generate hair (e.g., eyebrows and scalp hair) or sweat glands are significant clinical issues. In addition, in vitro skin models have been used for years in cosmetic and pharmaceutical companies for toxicology and drug screening, yet these models comprise only a rudimentary epidermis and dermis that does not produce sweat glands or hair follicles. Adult-onset hair loss is a widespread problem across all human populations, predominantly effecting men. Extreme genetic hair loss conditions, such as alopecia, affect both men and women. Few pharmacological, genetic, or cell therapies exist to treat hair loss. The skin has a complex cellular makeup that provides a functional barrier to outside pathogens and environmental insults. Since 1981, researchers have been able to recreate the basic 3D architecture of the skin using human skin equivalent (HSE) in vitro cultures. See Bell et al., Science 211, 1052-1054 (1981); Oh et al., The Journal of investigative dermatology 133, e14 (2013). HSEs minimally consist of a layer of dermal fibroblasts embedded in a collagen-based matrix and an overlying layer of epidermal keratinocytes. Today, HSEs created using these basic components are widely used in academia and industry to conduct investigations into skin diseases or skin care drugs. HSEs offer superior modeling of in vivo phenotypes, cellular signaling, cell migration, and drug responses compared to monolayer (i.e., two dimensional (2D)) cultures. However, the source of cell used to make HSEs is a chronic limitation of the technology. HSEs are often composed of primary cells derived from skin biopsies or leftover skin from surgical procedures. As a result of using limited or non-standardized tissue samples, the major cellular components of skin, keratinocytes and fibroblasts, need to be expanded in culture before use in HSEs. This process typically selects out less populous cells, such as Merkel cells or hair follicle bulge stem cells[2]. Although more standardized, HSEs constructed with immortalized keratinocytes or fibroblasts are similarly devoid of specialized cell types. No HSE model to date has successfully generated appendages (e.g., hair follicles and sweat glands) associated with normal skin.

Accordingly, there remains a need in the art, for efficient and reproducible methods for repairing and replacing damaged human skin and for reproducibly modeling in vivo skin phenotypes to develop therapies that do not suffer from side effects and limitations of current technologies, such as pharmaceutical compositions and current tissue engineering and skin grafting protocols using human skin equivalents that are incapable of generating hair.

SUMMARY OF THE INVENTION

In a first aspect, provided herein is a method of obtaining a three-dimensional multilayered skin composition. As described herein, the method comprises (a) culturing human pluripotent stem cell aggregates in a culture medium comprising Bone Morphogenetic Protein 4 (BMP4) and an inhibitor of Transforming Growth Factor Beta (TGFβ) signaling for about eight to about ten days, whereby non-neural epithelium (also known as surface ectoderm) forms within the aggregates; (b) embedding the cultured aggregates of (a) in a semi-solid culture medium comprising extracellular matrix; and (c) culturing the embedded aggregates of (b) for about 25 to about 30 days under conditions that promote self-assembly of cells within the embedded aggregates into three-dimensional, multilayered composition comprising an epidermal layer, a dermal layer, and a plurality of cells capable of forming a functional hair follicle is obtained. The inhibitor of TGFβ1-mediated signaling can be selected from the group consisting of SB431542 and A-83-01. The extracellular matrix can be a basement membrane extract (BME). The epidermal layer can be in direct contact with the dermal layer. The epidermal layer can comprise P63$^+$KRT5$^+$ epidermal keratinocytes. The dermal layer comprises follicle-initiating dermal papilla cells. The plurality of cells capable of forming a functional hair follicle can comprise cells selected from the group consisting of mesenchymal stem cells, dermal papilla cells, dermal sheath cells, and follicular epidermal stem cells.

In another aspect, the three-dimensional, multilayered engineered skin composition comprises an epidermal layer comprising in vitro-derived epidermal keratinocytes, a dermal layer comprising in vitro-derived dermal fibroblasts, and a plurality of cells capable of forming a functional hair follicle, wherein the epidermal layer and dermal layer are in direct contact. The plurality of cells capable of forming a functional hair follicle can comprise cells selected from the group consisting of mesenchymal stem cells, dermal papilla cells, dermal sheath cells, and follicular epidermal stem cells. The composition can further comprise at least one functional hair follicle and at least one functional sebaceous gland. The composition can further comprise a scaffold. The scaffold can be biodegradable or bioabsorbable. The composition can be capable of viable transplantation and engraftment into a human subject.

In a further aspect, provided herein is a method testing a compound for effects on hair growth or development, the method comprising exposing a test compound to the engineered skin composition as provided herein and detecting a change in hair growth or development.

These and other features, aspects, and advantages described herein will become better understood upon consideration of the following drawings, detailed description, and appended claims.

BRIEF DESCRIPTION OF THE DRAWINGS

FIGS. 12A-12H demonstrate skin organoid hair follicles have sebaceous glands, arrector pili muscles, stratum corneum, and bulge stem cells, comprising a complete pilosebaceous unit similar to fetal-stage hair. A, Schematic showing four specialized cellular compartments indicative of late-stage hair follicle development. Each cell population arises spontaneously in skin organoids. B-C, DIC images of a day 115 skin organoid with pigmented follicles. Pearl-like adipocytes are visible on the organoid surface. Near the infundibular region of the hair follicle (C) a sebaceous gland-like structure is visible stemming from the hair shaft. D, A cross section of the follicle in panel C shows that the sebaceous gland cells are lipid-rich (LipidTOX+) and have a sebaceous gland (sg)-like morphology. Adipocytes (ap) are also LipidTOX+ and have the classic morphology of hypodermal adipocytes. E, alpha-SMA+ ITGA8+ arrector pili muscle-like cells develop in association with organoid hair follicles. F-G, Low and high magnification images showing several hair follicles with KRT15+ patches reminiscent of hair follicle bulge stem cells. H, Filaggrin was expressed in the stratum corneum (sc) of skin organoid epidermis by day 120, denoting differentiation of basal epidermal keratinocytes.

DETAILED DESCRIPTION

Figure 1:
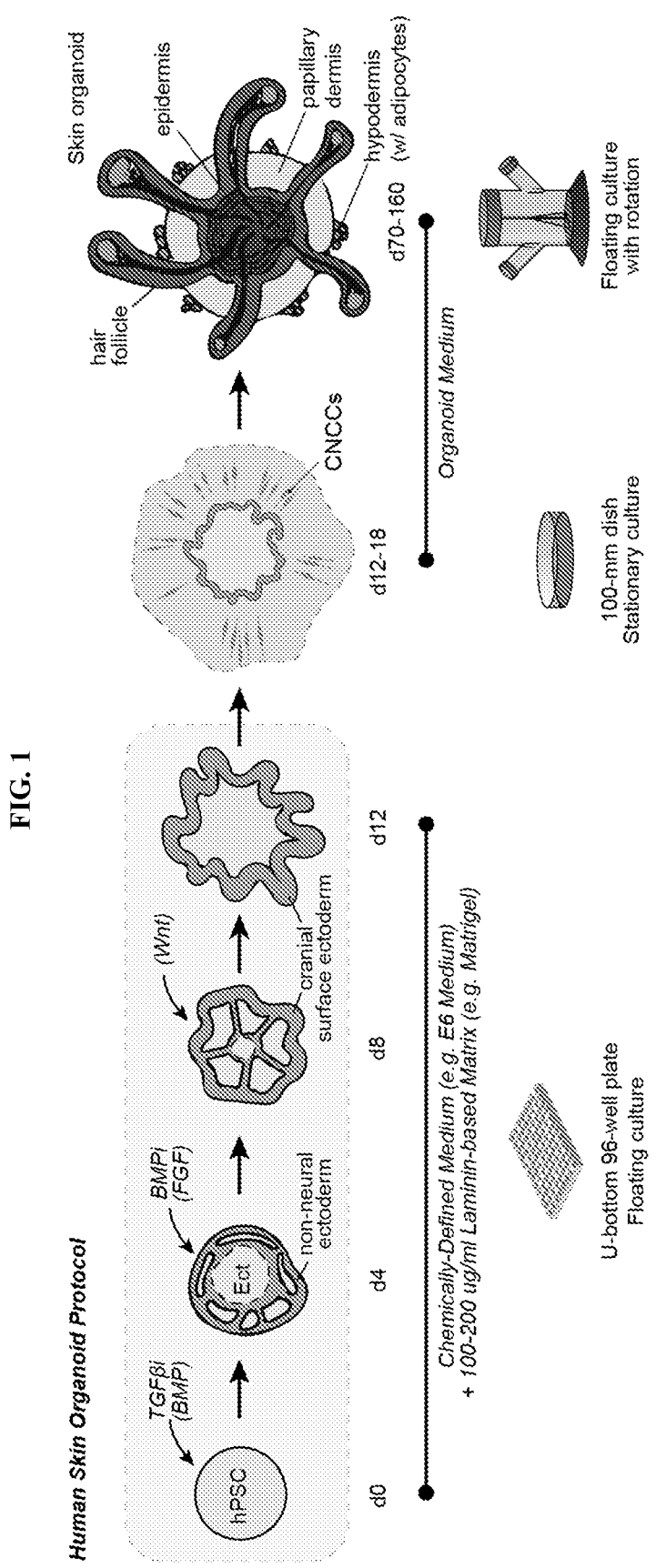
FIG. 1 is a schematic illustrating an exemplary protocol for deriving human skin organoids from human pluripotent stem cells (hPSCs). hPSC aggregates are cultured in a chemically-defined medium in the presence of extracellular matrix (ECM) components to produce a non-neural ectoderm (also known as surface ectoderm) epithelium. The surface ectoderm epithelium gives rise to both surface epithelial cells and cranial neural crest-like cells (CNCCs). In the second phase of culture, while floating in a chemically defined organoid medium, the CNCCs and epithelia self-organize into cysts having protruding hair follicles. Recommended culture formats are denoted under each step. The "floating culture with rotation" can be achieved using spinner flasks or 24-well plates placed on an in-incubator orbital shaker.

All publications, patents, and patent applications mentioned in this specification are herein incorporated by reference in their entirety as if each individual publication, patent, and patent application was specifically and individually indicated to be incorporated by reference.

The present invention is based at least in part on the Inventors' discovery that human pluripotent stem cell-derived precursor cells, when cultured in vitro under defined conditions that are permissive towards differentiation and remodeling, form highly uniform skin organoids that recapitulate the complexity and organization human skin and hair shafts. The Inventors further discovered that it was possible to produce complex human epidermis and dermis layers having the uniformity necessary for large-scale, quantitative in vitro modeling and screening applications.

Accordingly, the present invention relates to compositions including three-dimensional tissue constructs and cultures and methods of using such compositions as highly uniform models of human tissue and for screening drug candidates. In particular, provided herein are methods of efficiently and reproducibly producing and expanding complex, organized human epidermis and dermis comprising functional sweat glands and hair follicles suitable for in vivo transplantation, modeling genetic skin diseases and cancers, and useful as a screening platform for preclinical drug testing and other research applications.

An important advantage of the methods and systems provided herein is the ability to generate hairs from a single cell source. Although various cellular models for reconstituting skin in vitro are presently available, the methods and systems provided herein faithfully recapitulate in vivo development of complex, organized skin layers and generate hairs in vitro using only human cells. The present invention provides an important opportunity to study these cells in an in vitro human model. In addition, the present invention is useful for identifying materials and combinatorial strategies for human tissue engineering. The present invention also provides methods of using skin organoids and three-dimensional tissue constructs comprising the same as highly uniform models of human tissue and for screening potentially therapeutic or toxic agents. Among the advantages offered by the present invention, skin organoids of the invention provide biologically-relevant information about the effects of various agents within the complex environment of human skin. In addition, the skin organoid derivation methods provided herein are chemically-defined, efficient (one cell aggregate can produce 10 to 30 or more hair follicles), and mimic normal embryonic developmental timing, with folliculogenesis occurring after ~60 days in culture; equivalent to the $10^{th}$ week of human embryonic development. Moreover, the methods produce skin organoids exclusively from the ectoderm germ layer and, since the dermis is derived from cranial neural crest cells, the resulting skin is representative of cranial skin. Finally, the present invention employs materials that support a wide diversity of skin cells and offers combinatorial strategies for various in vitro human tissue engineering systems.

Methods

As described herein, this disclosure provide methods for generating skin tissue from human pluripotent stem cells. In exemplary embodiments, the methods provided herein producing skin organoid cultures that recapitulate in vivo tissue structural organization, complexity, functional differentiation, chemical and mechanical signals, and therefore, may be more physiologically relevant than 2D cultures of primary or immortalized cells. As used herein, the term "skin organoid" refers to a tissue-like structure (i.e., exhibiting structural properties of a particular tissue type) that resembles a whole organ and is assembled in vitro by the separate addition and self-organization of various cell types including, but not limited to, pluripotent stem cells, fetal neural stem cells, and isolated organ progenitors. See, e.g., Lancaster and Knoblich, *Science* 345(6194) (2014). Preferably, skin organoids obtained according to the methods of this disclosure are multi-layered (e.g., comprising human epidermis and dermis) in vitro skin models that both histologically as well as functionally correspond substantially to native skin. As described in the paragraphs that follow, the methods of this disclosure produce skin organoid cultures that recapitulate the complexity and organization human skin and hair shafts by differentiating human pluripotent stem cells under conditions that promote differentiation of the pluripotent stem cells into non-neural epithelium and cranial neural crest cells and, subsequently, epidermis and dermis tissue layers suitable for hair-producing skin grafts. In some cases, skin organoids obtained according to the methods of this disclosure further comprise hair follicles having one or more specialized cellular compartments or cell types such as sebaceous glands, eccrine glands, melanocytes, sensory neurons, fat cells similar to subcutaneous fat, hair follicle bulge stem cells, and Merkel progenitor cells.

In a first aspect, a method of obtaining a human skin organoid comprises aggregating human pluripotent stem cells into spheroid aggregates and culturing the spheroid aggregates in the presence of small molecules and recombinant transcription factors and other proteins, whereby the pluripotent cells are induced to differentiate into a multi-layered tissue of epidermis and dermis capable of generating hair. Referring to FIG. 1, the method comprises aggregating human pluripotent stem cells into spheroid aggregates and culturing the spheroid aggregates in the presence of a chemically defined culture medium and extracellular matrix (ECM) components, in addition to factors that promote non-neural induction. In such cases, the chemically culture medium can comprise or consist essentially of the following defined components: a chemically defined basal cell culture medium, an agonist (activator) of Bone Morphogenetic Protein signaling, and an inhibitor of transforming growth factor beta (TGFβ) signaling (see "TGFi" in FIG. 1). When cultured according to these steps, at least a subset of the aggregated human pluripotent stem cells are induced to differentiate to form a core of mesodermal cells within each aggregate. Preferably, aggregates comprising a core of mesodermal cells are cultured in the presence of an agonist of BMP signaling (e.g., bone morphogenetic protein-4 (BMP4)) and an inhibitor of TGFβ signaling ("TGFi") for about 8 days to about 10 days.

Following the culture of about 8 days to about 10 days, cells of the mesodermal core migrate to the surface of the aggregates and produce a layer of non-neural ectoderm that lines the core of the aggregate and cranial neural crest-like cells (CNCCs). Referring again to FIG. 1, following 12-18 days in culture, the CNCCs migrate to the aggregate surface and form a mesenchyme. By 30 days of culture, the ectoderm and mesenchymal cells produce skin organoids containing basal keratinocytes and dermal fibroblasts. Remarkably, after about 75 days to about 120 days (e.g., about 75, 80, 85, 90, 95, 100, 105, 110, 115, 120 days) in culture the derived skin produces outward growing hair follicles. In contrast to normal embryonic skin, the skin organoids obtained according to the methods of this disclosure form a cyst with concentric layers of keratinocytes (in an inner layer) and fibroblasts (in an outer layer). The skin and follicles are equipped with many specialized cellular compartments seen in normal skin, such as sensory neurons, sebaceous glands, subcutaneous fat, pigmented melanocytes, and touch-receptive Merkel cells.

In exemplary embodiments, the agonist of BMP signaling is selected from the group consisting of BMP4, BMP2, and BMP7. Alternatively, the agonist of BMP signaling is any protein or small molecule that mimics the downstream signaling cascade of a BMP binding to its receptors by causing phosphorylation of Smad1/5/8. While TGFβ-1 and Activin A are agonists of TGFβ signaling, TGFβ signaling can be antagonized using, for example, the small molecule inhibitor SB-431542 ("SB"), which is a potent and selective inhibitor of ALK5. Other inhibitors/antagonists of TGFβ signaling include, without limitation, SB525334 (a selective inhibitor of TGFβ Receptor I), RNAi nucleic acids specific for one or more TGFβ receptors, and anti-TGFβ antibodies.

In a next step, aggregates cultured in the presence of the agonist of BMP signaling and the inhibitor of TGFβ signaling are embedded into a semi-solid culture medium comprising extracellular matrix (ECM) components. The embedded aggregates are cultured under conditions that promote directed differentiation of the non-neural ectoderm epithelium and neural crest-like cells into epidermis and mesenchyme comprising dermal fibroblasts. Preferably, the embedded aggregates are cultured for about 25 to about 30 days under conditions that promote self-assembly of cells within the embedded aggregates into three-dimensional, multilayered skin composition comprising an epidermal layer, a dermal layer, and a plurality of cells capable of forming a functional hair follicle is obtained. The resulting skin composition comprises two tissue layers (epidermis and dermis) that develop in concert to form full-thickness skin comprising functional hair follicles. Cells capable of forming a functional hair follicle include, without limitation, follicle-specific mesenchymal stem cells, dermal papilla cells, dermal sheath cells, and follicular epidermal stem cells.

Preferably, human pluripotent stem cells are cultured in a chemically-defined basal culture medium formulation comprising defined components. In some cases, the chemically defined basal culture medium is the culture medium "DF3S" as set forth in Chen et al., *Nature Methods* 8:424-429 (2011), which is incorporated by reference herein as if set forth in its entirety. In other cases, the chemically defined basal culture medium is E6, E7, or E8 culture medium. As used herein, the terms "E7 culture medium" and "E7" are used interchangeably and refer to a chemically defined culture medium comprising or consisting essentially of DF3S supplemented to further comprise insulin (20 µg/mL), transferrin (10.67 ng/mL) and human Fibroblast Growth Factor 2 (FGF2) (100 ng/mL). As used herein, the terms "E8 culture medium" and "E8" are used interchangeably and refer to a chemically defined culture medium comprising or consisting essentially of DF3S supplemented by the addition of insulin (20 µg/mL), transferrin (10.67 ng/mL), human FGF2 (100 ng/mL), and human TGFβ1 (Transforming Growth Factor Beta 1) (1.75 ng/mL). As an alternative, E8 medium is also available from Thermal Fisher/Life Technologies Inc. as Essential 8, or from Stem Cell Technologies as "TeSR®-E8." As used herein, the terms "E6 culture medium" and "E6" are used interchangeably and refer to a chemically defined culture medium comprising or consisting essentially of DF3S supplemented by the addition of insulin (20 µg/mL), and transferrin (10.67 ng/mL). E6 is similar to E8 medium but without FGF2 and TGF-β. The medium can be prepared based on the formula in previous publication (Chen et al., *Nature Methods* 8:424-429, 2011). Similar medium is available from Thermal Fisher/Life Technologies Inc. as Essential 6, or from Stem Cell Technologies as "TeSR®-E6."

A confluent culture of pluripotent stem cells can be chemically, enzymatically or mechanically dissociated from a surface, such as Matrigel® or a chemically defined substrate (e.g., a hydrogel), into clumps, aggregates, or single cells. In exemplary embodiments, the dissociated cells (as clumps, aggregates, or single cells) are plated onto a surface in a protein-free basal medium such as Dulbecco's Modified Eagle's Medium (DMEM)/F12, mTeSR™ (StemCell Technologies; Vancouver, British Columbia, Canada), and TeSR™. The full constituents and methods of use of TeSR™ are described in Ludwig et al. See, e.g., Ludwig T, et al., "Feeder-independent culture of human embryonic stem cells," *Nat. Methods* 3:637-646 (2006); and Ludwig T, et al., "Derivation of human embryonic stem cells in defined conditions," *Nat. Biotechnol.* 24:185-187 (2006), each of which is incorporated herein by reference as if set forth in its entirety. Other DMEM formulations suitable for use herein include, e.g., X-Vivo™ (BioWhittaker, Walkersville, Md.) and StemPro® (Invitrogen; Carlsbad, Calif.).

In recent years, polyethylene glycol (PEG)-based hydrogels cross-linked with defined concentrations of extracellular matrix proteins have become a chemically-defined alternative to poorly defined matrices such as Matrigel®. In exemplary embodiments of the invention, therefore, the methods provided herein can comprise embedding or encapsulation of cells in a chemically defined, porous biomaterial such as a hydrogel. The term "hydrogel" refers to a highly hydrated porous material comprising synthetic or biological components formed when an organic polymer (natural or synthetic) is cross-linked via covalent, ionic, or hydrogen bonds to create a 3D open-lattice structure that entraps water molecules to form a gel. Hydrogels appropriate for constructing 3D skin organoids of the present invention include, without limitation, synthetic hydrogels, bioactive hydrogels, biocompatible hydrogels, cytocompatible hydrogels, chemically defined hydrogels, chemically-defined synthetic hydrogels, and proteolytically degradable hydrogels. As used herein, "bioactive" is intended to indicate the ability to facilitate a cellular or tissue response, such as differentiation of a pluripotent stem cell, induction of vasculogenesis, neural stem cell differentiation, promotion of cellular attachment, promotion of cell self-assembly, and promotion of cell-cell interactions. As used herein, the term "biocompatible" refers to the ability of a polymer or hydrogel to perform as a substrate that will support cellular activity, including the facilitation of molecular and mechanical signaling systems, in order to permit proper cell self-assembly or cellular function such as tissue formation, production of soluble bioactive molecules (e.g., growth factors), specific cell behaviors such as migration and proliferation. In some cases, "biocompatibility" means the absence of components having cell- or tissue-damaging effects. As used herein, the term "cytocompatible" means the hydrogel material is substantially non-cytotoxic and produces no, or essentially no, cytotoxic degradation products, while the term "proteolytically degradable" as used herein means that the crosslinked backbone can be cleaved enzymatically or non-enzymatically to break down the scaffold network.

As used herein, the term "chemically defined" means that the identity and quantity of each component of a composition (e.g., a hydrogel) is known. An important goal in the fields of pluripotent stem cell culture and directed differentiation of pluripotent stem cells is to develop culture materials and culture media that provide improved performance consistency and reproducibility. In some cases, a chemically defined hydrogel for use in deriving a skin organoid of this disclosure comprises a minimal number of defined components/ingredients.

In some cases, it can be advantageous to add exogenous cells to a skin organoid or in vitro tissue construct comprising a skin organoid obtained according to the methods provided herein, such that the resulting composition comprises cell types not derived according to the methods of this disclosure but advantageous for recapitulating in vivo skin and for providing the skin organoid with additional structural complexity. For example, a tissue construct can be seeded with epidermal immune cells (e.g., Langerhan's cells), mesoderm-derived cells types (e.g., colony-forming endothelial cells for blood vessel formation as described by Prasain et al., *Nature Biotech* 32, 1151-1157 (2014)), or endothelial cells. Cells for seeding skin organoids can be obtained from natural tissue or derived according to other in vitro derivation protocols. For example, endothelial colony forming cells derived from hiPSCs have been shown to efficiently generate vasculature under a variety of in vitro and in vivo conditions (Dr. Mervin Yoder, personal communication).

A hydrogel appropriate for use according to the methods provided herein can be prepared using various polymers including, without limitation, poly(ethylene glycol) (PEG), polyvinyl alcohol (PVA), polyvinyl pyrrolidone (PVP), polyacrylamides, and polysaccharides. PEG is a polymer having solubility in water and in many organic solvents and, generally, lacking toxicity, antigenicity, or immunogenicity. PEG can be activated at each terminus to be bifunctional. In other cases, one terminus can be modified to have a reactive moiety. For example, a PEG monomer can be modified to have a relatively inert methoxy moiety (e.g., methoxy-PEG- OH) at one terminus while the other terminus is a hydroxyl group that is readily chemically modifiable. Polysaccharide hydrogels are made by crosslinking natural or semi-synthetic polysaccharides such as alginate, carboxymethylcellulose, hyaluronic acid, and chitosan. The cross-linking reaction allows for the formation of a three-dimensional network made of covalent bonds between the polymer chains—a network that is stable under physiological conditions.

In some embodiments, a hydrogel appropriate for use according to the methods provided herein is at least partially contained within a three-dimensional structural framework. Preferably, a structural framework comprises a three dimensional structure prepared from one or more polymeric materials, including biopolymers.

As used herein, "pluripotent stem cells" appropriate for use according to a method of the invention are cells having the capacity to differentiate into cells of all three germ layers. Suitable pluripotent cells for use herein include human embryonic stem cells (hESCs) and human induced pluripotent stem (iPS) cells. As used herein, "embryonic stem cells" or "ESCs" mean a pluripotent cell or population of pluripotent cells derived from an inner cell mass of a blastocyst. See Thomson et al., *Science* 282:1145-1147 (1998). These cells express Oct-4, SSEA-3, SSEA-4, TRA-1-60, and TRA-1-81, and appear as compact colonies having a high nucleus to cytoplasm ratio and prominent nucleolus. ESCs are commercially available from sources such as WiCell Research Institute (Madison, Wis.). As used herein, "induced pluripotent stem cells" or "iPS cells" mean a pluripotent cell or population of pluripotent cells that may vary with respect to their differentiated somatic cell of origin, that may vary with respect to a specific set of potency-determining factors and that may vary with respect to culture conditions used to isolate them, but nonetheless are substantially genetically identical to their respective differentiated somatic cell of origin and display characteristics similar to higher potency cells, such as ESCs, as described herein. See, e.g., Yu et al., *Science* 318:1917-1920 (2007).

Induced pluripotent stem cells exhibit morphological properties (e.g., round shape, large nucleoli and scant cytoplasm) and growth properties (e.g., doubling time of about seventeen to eighteen hours) akin to ESCs. In addition, iPS cells express pluripotent cell-specific markers (e.g., Oct-4, SSEA-3, SSEA-4, Tra-1-60 or Tra-1-81, but not SSEA-1). Induced pluripotent stem cells, however, are not immediately derived from embryos. As used herein, "not immediately derived from embryos" means that the starting cell type for producing iPS cells is a non-pluripotent cell, such as a multipotent cell or terminally differentiated cell, such as somatic cells obtained from a post-natal individual.

Human iPS cells can be used according to a method described herein to obtain skin organoids having the genetic complement of a particular human subject. For example, it may be advantageous to obtain skin organoids that exhibit one or more specific phenotypes associated with or resulting from a particular disease or disorder of the particular mammalian subject. In such cases, iPS cells are obtained by reprogramming a somatic cell of a particular human subject according to methods known in the art. See, for example, Yu et al., *Science* 324(5928):797-801 (2009); Chen et al., *Nat. Methods* 8(5):424-9 (2011); Ebert et al., *Nature* 457(7227): 277-80 (2009); Howden et al., *Proc. Natl. Acad. Sci. U.S.A* 108(16):6537-42 (2011).

In particular, the methods provided herein are useful for obtaining induced pluripotent stem cell (iPSC)-derived skin organoids suitable for autologous skin grafts and other clinical and research applications. For example, iPSC-derived epidermis and dermis obtained as provided herein can be used to model drug responses using an in vitro skin organoid that recapitulates skin layers in an individual having, for example, a particular disease. Accordingly, subject-specific iPSC-derived skin organoids have particular utility for identifying genetic factors and epigenetic influences that contribute to variable drug responses between human subjects.

Subject-specific somatic cells for reprogramming into induced pluripotent stem cells can be obtained or isolated from a target tissue of interest by biopsy or other tissue sampling methods. In some cases, subject-specific cells are manipulated in vitro prior to use in a three-dimensional tissue construct of the invention. For example, subject-specific cells can be expanded, differentiated, genetically modified, contacted to polypeptides, nucleic acids, or other factors, cryo-preserved, or otherwise modified prior to introduction to a three-dimensional tissue construct.

Preferably, human pluripotent stem cells (e.g., human ESCs or iPS cells) are cultured under chemically defined conditions and in the absence of a feeder layer (e.g., a fibroblast layer), a conditioned medium, or a culture medium comprising poorly defined or undefined components. As used herein, the terms "chemically defined medium" and "chemically defined cultured medium" also refer to a culture medium containing formulations of fully disclosed or identifiable ingredients, the precise quantities of which are known or identifiable and can be controlled individually. As such, a culture medium is not chemically defined if (1) the chemical and structural identity of all medium ingredients is not known, (2) the medium contains unknown quantities of any ingredients, or (3) both. Standardizing culture conditions by using a chemically defined culture medium minimizes the potential for lot-to-lot or batch-to-batch variations in materials to which the cells are exposed during cell culture. Accordingly, the effects of various differentiation factors are more predictable when added to cells and tissues cultured under chemically defined conditions. As used herein, the term "serum-free" refers to cell culture materials that are free of serum obtained from animal (e.g., fetal bovine) blood. In general, culturing cells or tissues in the absence of animal-derived materials (i.e., under conditions free of xenogeneic material) reduces or eliminates the potential for cross-species viral or prion transmission.

In some cases, pluripotent stem cell aggregates are cultured in the presence of a kinase inhibitors, such as Rho-kinse (ROCK) inhibitor. ROCK inhibitors are known to protect single cells and small aggregates of cells. See, e.g., US Patent Application Publication No. 2008/0171385, incorporated herein by reference as if set forth in its entirety; and Watanabe K, et al., "A ROCK inhibitor permits survival of dissociated human embryonic stem cells," *Nat. Biotechnol.* 25:681-686 (2007). ROCK inhibitors are shown below to significantly increase pluripotent cell survival on chemically defined surfaces. ROCK inhibitors suitable for use herein include, but are not limited to, (S)-(+)-2-methyl-1-[(4-methyl-5-isoquinolinyl)sulfonyl]homopiperazine dihydrochloride (informal name: H-1152), 1-(5-isoquinolinesulfonyl)piperazine hydrochloride (informal name: HA-100), 1-(5-isoquinolinesulfonyl)-2-methylpiperazine (informal name: H-7), 1-(5-isoquinolinesulfonyl)-3-methylpiperazine (informal name: iso H-7), N-2-(methylamino) ethyl-5-isoquinoline-sulfonamide dihydrochloride (informal name: H-8), N-(2-aminoethyl)-5-isoquinolinesulphonamide dihydrochloride (informal name: H-9), N-[2-p-bromo-cinnamylamino)ethyl]-5-isoquinolinesulfonamide dihydrochloride (informal name: H-89), N-(2-guanidinoethyl)-5-isoquinolinesulfonamide hydrochloride (informal name: HA-1004), 1-(5-isoquinolinesulfonyl) homopiperazine dihydrochloride (informal name: HA-1077), (S)-(+)-2-Methyl-4-glycyl-1-(4-methylisoquinolinyl-5-sulfonyl)homopiperazine dihydrochloride (informal name: glycyl H-1152) and (+)-(R)-trans-4-(1-aminoethyl)-N-(4-pyridyl)cyclohexanecarboxamide dihydrochloride (informal name: Y-27632). The kinase inhibitor can be provided at a concentration sufficiently high that the cells survive and remain attached to the surface. An inhibitor concentration between about 3 µM to about 10 µM can be suitable. At lower concentrations, or when no ROCK inhibitor is provided, undifferentiated cells typically detach, while differentiated cells remain attached to the defined surface.

In another aspect, provided herein is a method for producing skin organoids comprising hair follicles with and without pigmentation. As described in the Examples that follow, generation of melanocytes in hPSC-derived skin organoids is dependent on the presence of active canonical Wnt signaling between days 8 and days 12 of the skin organoid derivation methods described in this disclosure. Accordingly, this disclosure provides methods for producing skin organoids that lack pigmented hair follicles (e.g., comprise albino hair follicles) as well as methods for producing skin organoids that possess pigmented hair follicles. Any appropriate method for activating canonical Wnt signaling between days 8 and 12 can be used. For example, the method can comprise contacting the hPSC aggregates to an agonist of canonical Wnt signaling. Wnt agonists include, without limitation, inhibitors of the molecule Glycogen Synthase Kinase 3 (GSK3). For example, CHIR-99021 is a small molecule inhibitor of the molecule Glycogen Synthase Kinase 3 (GSK3) and, consequently, a potent agonist of canonical Wnt signaling. In some cases, it will be advantageous to obtain skin organoids comprising non-pigmented (albino) hair follicles and then seeding such skin organoids using melanocytes obtained from a donor or donors having various skin and hair colors.

In another aspect, provided herein is a method for obtaining a pure or substantially pure population of epidermal keratinocytes from hPSCs.

In a further aspect, provided herein is a method of generating different types of human skin tissue using the three-dimensional skin organoid model described herein.

Any appropriate method can be used to detect expression of biological markers characteristic of cell types described herein. For example, the presence or absence of one or more biological markers can be detected using, for example, RNA sequencing, immunohistochemistry, polymerase chain reaction, qRT-PCR, or other technique that detects or measures gene expression. In exemplary embodiments, a cell population obtained according to a method provided herein is evaluated for expression (or the absence thereof) of biological markers of pre-non-neural ectoderm such as AP2. Quantitative methods for evaluating expression of markers at the protein level in cell populations are also known in the art. For example, flow cytometry is used to determine the fraction of cells in a given cell population that express or do not express biological markers of interest. As described in the Examples section below, differentiation of human pluripotent stem cells into multilayered skin organoids according to methods of the present invention can be confirmed based on the absence of non-dermal cell types such as chondrocytes and neurons and the presence of cells having epidermal or dermal identity. Differentiated cell identity is also associated with downregulation of pluripotency markers such as NANOG and OCT4 (relative to human ES cells or induced pluripotent stem cells).

Any appropriate method or methods can be used to confirm uniformity and the presence or absence of certain components in a skin organoid or skin organoid-containing tissue construct provided herein. For example, one may detect expression of biological markers characteristic of the cell types described herein. Suitable methods for detecting the presence or absence of biological markers are well known in the art and include, without limitation, immunohistochemistry, qRT-PCR, RNA sequencing, and the like for evaluating gene expression at the RNA level. In some cases, methods such as immunohistochemistry are used to detect and identify cell types or biomolecules within a skin organoid or skin organoid-containing tissue construct. For example, whole tissue constructs or portions thereof can be stained for specific differentiation markers by immunohistochemistry. In some cases, it will be advantageous to perform dual-label immunofluorescence to assess the relative expression of individual marker proteins or to detect multiple progenitor or differentiated cell types within a construct. Appropriate primary and secondary antibodies are known and available to those practicing in the art. Quantitative methods for evaluating expression of markers at the protein level in cell populations are also known in the art. For example, flow cytometry is used to determine the fraction of cells in a given cell population that express or do not express biological markers of interest. In some cases, it will be advantageous to fix or freeze skin organoids or tissue constructs of the invention for histology or microscopy. For example, skin organoids of the invention can be fixed in formalin or paraformaldehyde for plastic embedment and sectioning using routine methods. In exemplary embodiments, confocal microscopy can reveal the distribution of cell types and structures throughout a three-dimensional tissue construct of the invention. In some cases, a three-dimensional assembly of images obtained by confocal microscopy is used to analyze the distribution and organization of various cells and structures.

Compositions

In another aspect, provided herein are three-dimensional, multilayered in vitro-derived skin organoids obtained according to the methods provided herein. Also provided are three-dimensional (3D) tissue constructs or tissue compositions comprising skin organoids obtained as described herein and engineered materials. For example, a 3D tissue construct can be obtained by differentiating aggregates of pluripotent stem cells according to the methods described in this disclosure in a collagen-based substrate, whereby cells differentiating under such culture conditions self-organize into dermal and epidermal layers that are in contact with each other and capable of producing hair. In some cases, a 3D tissue construct of the present invention further comprises isolated biological components. As used herein, an "isolated" biological component (such as a protein or organelle) has been substantially separated or purified away from other biological components in the cell of the organism in which the component naturally occurs, such as other chromosomal and extra-chromosomal DNA and RNA, proteins, and organelles. As used herein, the term "isolated protein" includes proteins purified by standard purification methods. The term also embraces proteins prepared by recombinant expression in a host cell, as well as chemically synthesized proteins, or fragments thereof.

In some cases, a skin organoid or 3D tissue construct comprising a skin organoid is provided with or incorporated onto or into a support structure for construction of a new tissue. Support structures can be scaffolds, meshes, solid supports, tubes, porous structures, and/or a hydrogel. A support structure can be a tissue engineering scaffold, matrix, or material forming a matrix. Support structures can be biodegradable or non-biodegradable, in whole or in part. As used herein, the term "biodegradable" means that a material degrades or breaks down into its component subunits by a biochemical process. The support can be formed of a natural or synthetic polymer, metal such as titanium, bone or hydroxyapatite, or a ceramic. Natural polymers include, without limitation, collagen, hyaluronic acid, polysaccharides, and glycosaminoglycans. Synthetic polymers include, without limitation, polyhydroxyacids such as polylactic acid, polyglycolic acid, and copolymers thereof, polyhydroxyalkanoates such as polyhydroxybutyrate, polyorthoesters, polyanhydrides, polyurethanes, polycarbonates, and polyesters.

Although human cells are preferred for use in the invention, the cells to be used in tissue constructs of the invention are not limited to cells from human sources. Cells from other mammalian species including, but not limited to, equine, canine, porcine, bovine, feline, caprine, murine, and ovine sources can be used. Cell donors may vary in development and age. Cells can be derived from donor tissues of embryos, neonates, or older individuals including adults.

In some cases, a skin organoid of the present invention may comprise recombinant or genetically-modified cells in place of or in addition to unmodified or wild-type ("normal") cells. For example, it can be advantageous in some cases to include recombinant and genetically-modified cells that produce recombinant cell products, growth factors, hormones, peptides or proteins (e.g., detectable reporter proteins) for a continuous amount of time or as needed when biologically, chemically, or thermally signaled due to the conditions present in culture. Procedures for obtaining recombinant or genetically modified cells are generally known in the art, and are described in Sambrook et al, *Molecular Cloning, A Laboratory Manual*, Cold Spring Harbor Press, Cold Spring Harbor, N.Y. (1989), incorporated herein by reference.

In a particular embodiment, iPS cells comprising a detectable reporter gene (e.g., a fluorescent reporter gene, a reporter gene for colorimetric detection) can be used to derive skin organoids having, for example, fluorescently labeled hair follicle bulge stem cells and dermal papilla cells. Such skin organoids would be advantageous to rapidly assess hair follicle cycle stage during drug testing. As described in the Examples that follow (see FIGS. 14B-14D), a CRISPR/Cas9 methodology can be used to generate iPS cells comprising a target reporter construct. In some cases, it will be advantageous to obtain iPS cells comprising a dual reporter system in which different cell types are labeled with different reporter proteins for rapid identification and cell tracking. By way of example, iPSC-derived skin organoids can be obtained wherein enhanced Green Fluorescent Protein (eGFP) or another GFP or GFP variant is used to label hair follicle bulge stem cells and a tdTomato reporter construct is used to label dermal papilla cells and/or Merkel progenitor cells.

Figure 15A:
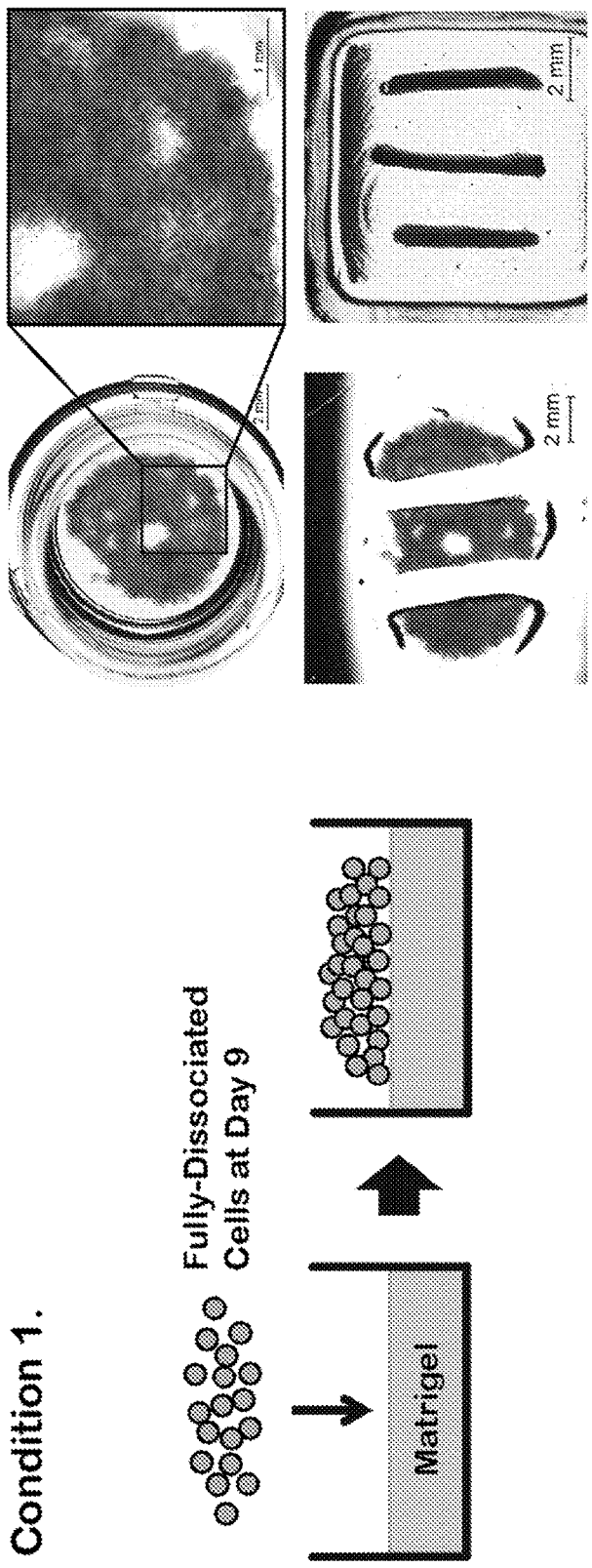
FIG. 15A-15B demonstrate skin organoids can be dissociated and embedded in a porous matrix without losing the ability to form organized epidermal and dermal tissue. Fully dissociating day 9 organoids and re-plating dissociated cells on a layer of Matrigel (A, Condition 1) or in a droplet of cell and Matrigel mixture (B, Condition 2) led to formation of a large layer of keratinocytes or many individual keratinocyte cysts, respectively.
Figure 15B:
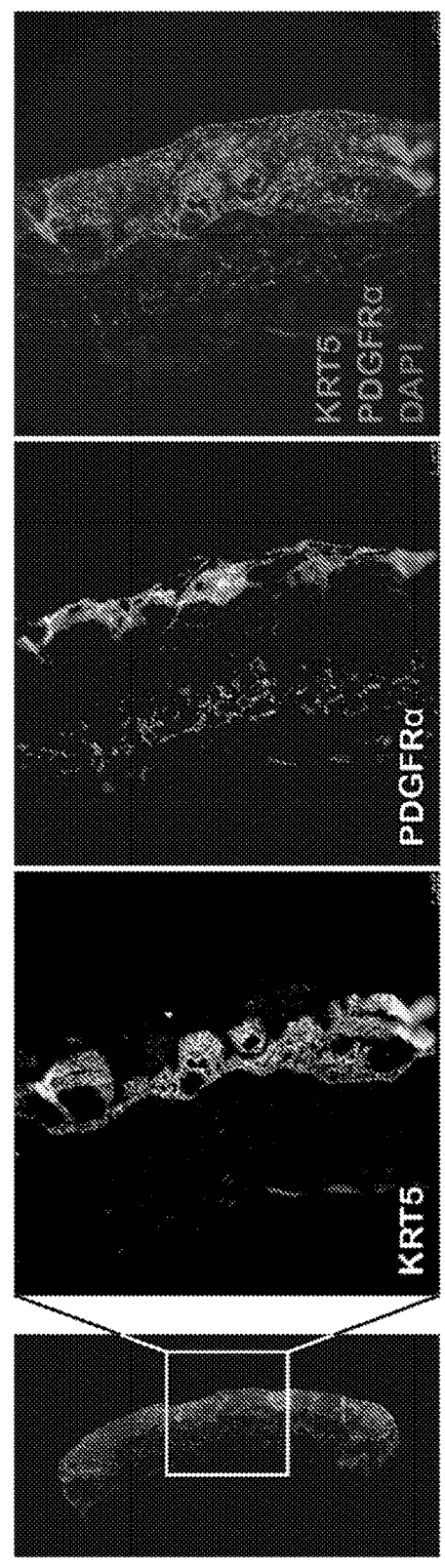

In another aspect, provided herein is a composition comprising an artificial skin matrix (or matrices) and mechanically or enzymatically dissociated skin organoids obtained according to the methods of this disclosure (see FIGS. 15A-15B). Such compositions can be used to generate hair-bearing skin grafts. Artificial skin matrices suitable for use in these compositions include, without limitation, the bilayer matrix wound dressing Integra™ (Integra LifeSciences Corp.) and Oasis® wound matrix (Smith & Nephew, Inc.), which is derived from porcine porcine small intestinal submucosa (SIS). To obtain such composition, skin organoids can be mechanically or enzymatically dissociated using any appropriate methods, or using a combination of mechanical and enzymatic dissociation methods. Mechanical dissociation or separation of a skin organoid can be accomplished by trituration with a pipette tip, sonication, vortex disaggregation, use of a cell scraper, or forced filtration through a mesh or sieve. Enzymatic dissociation can be accomplished by using one or more enzyme-based dissociation reagents, such as dispase, Accutase, and TrypLE. Preferably, the enzyme-based dissociation reagent is Accutase. An EDTA-PBS solution could also be used for dissociation.

In another aspect, the present invention provides human skin organoids comprising one or more cell types derived from a particular mammalian subject (e.g., a particular human subject). In some cases, one or more cell types derived exhibit one or more specific phenotypes associated with or resulting from a particular disease or disorder of the particular mammalian subject. Subject-specific cells can be obtained or isolated from a target tissue of interest by biopsy or other tissue sampling methods. In some cases, subject-specific cells are manipulated in vitro prior to use in a tissue construct of the invention. For example, subject-specific cells can be expanded, differentiated, genetically modified, contacted to polypeptides, nucleic acids, or other factors, cryo-preserved, or otherwise modified prior to use in a tissue construct of the present invention. In some cases, subject-specific cells are differentiated prior to, during, or after seeding onto or into a skin organoid obtained according to the methods described herein. In other cases, subject-specific cells for use in a skin organoid of the invention are induced pluripotent stem cells obtained by reprogramming somatic cells of the subject according to methods known in the art. See, for example, Yu et al., *Science* 324(5928):797-801 (2009); Chen et al., *Nat Methods* 8(5):424-9 (2011); Ebert et al., *Nature* 457(7227):277-80 (2009); Howden et al., *Proc Natl Acad Sci USA* 108(16):6537-42 (2011). Human induced pluripotent stem cells allow modeling of drug responses in a genetically diverse population of individuals, including those individuals with genetic diseases. Even the safest drugs may cause adverse reactions in certain individuals with a specific genetic background or environmental history. Accordingly, skin organoids comprising cells derived from iPS cells obtained from individuals having known susceptibilities or resistances to various drugs or diseases will be useful in identifying genetic factors and epigenetic influences that contribute to variable drug responses.

As to the compositions described herein, three-dimensional skin organoids and engineered skin products can be transplanted to a subject using any transplantation methods generally known in the art. In addition to use for skin graft transplantation, hPSC-derived skin organoids obtained according to the methods provided herein are useful as in vitro models for screening possible therapeutic agents. Other applications of hPSC-derived skin organoids obtained according to the methods provided herein include, without limitation, use of the skin organoids as an in vitro model to study the etiology of and/or to identify new treatments for a host of skin disorders, such as psoriasis, alopecia, ectodermal dysplasias, monilethrix, Netherton syndrome, and skin cancers (e.g., Merkel cell carcinoma). The manner in which a test compound has an effect on a particular biological activity of the skin organoids of the present invention will depend on the nature of the test compound, the particular composition of the skin organoid or tissue construct, and the particular biological activity being assayed. However, methods of the present invention will generally include the steps of (a) culturing a skin organoid as provided herein in the presence of a test compound, (b) assaying a selected structure or functional attribute of the skin organoid following exposure to the test compound, and (c) comparing values determined in the assay to the values of the same assay performed using a skin organoid having the same composition as the organoid cultured in the presence of the test compound but cultured in the absence of the test compound (or in the presence of a control). Detecting a positive or negative change in a biological property (structural or functional) of a cell of the skin organoid can comprise detecting at least one effect of a test compound on morphology or life span of a cell or tissue within the contacted organoid. In some cases, detecting comprises performing a method such as RNA sequencing, gene expression profiling, transcriptome analysis, metabolome analysis, detecting reporter or sensor, protein expression profiling, Førster resonance energy transfer (FRET), metabolic profiling, and microdialysis. Test compounds can be screened for effects on gene expression in the contacted tissue construct, where differential gene expression as compared to an uncontacted tissue construct is detected.

In a further aspect, provided herein is a commercial grade iPSC-derived skin tissue, where the commercial grade skin tissue is obtained according to the methods provided herein. The commercial grade composition can be a 3D multilayered engineered skin construct that, in some cases, is incorporated into or onto a support structure (e.g., an artificial skin matrix) as described herein.

The human skin organoids and commercial grade iPSC-derived skin tissues described herein can be useful for various in vitro and in vivo applications. Preparations for use in clinical applications must be obtained in accordance with regulations imposed by governmental agencies such as the U.S. Food and Drug Administration. Accordingly, in exemplary embodiments, the methods provided herein are conducted in accordance with Good Manufacturing Practices (GMPs), Good Tissue Practices (GTPs), and Good Laboratory Practices (GLPs). Reagents comprising animal derived components are not used, and all reagents are purchased from sources that are GMP-compliant. In the context of clinical manufacturing of a bioengineered iPSC-derived skin tissue for use in humans, GTPs govern cell donor consent, traceability, and infectious disease screening, whereas GMPs are relevant to the facility, processes, testing, and practices to produce consistently safe and effective products for human use. See Lu et al. *Stem Cells* 27: 2126-2135 (2009). Where appropriate, oversight of patient protocols by agencies and institutional panels is envisioned to ensure that informed consent is obtained; safety, bioactivity, appropriate dosage, and efficacy of products are studied in phases; results are statistically significant; and ethical guidelines are followed.

Article of Manufacture

In another aspect, provided herein is a kit comprising one or more components useful for obtaining a three-dimensional (3D), multilayered in vitro skin composition. Components of the kit can include one or more small molecule inhibitors of a signal transduction pathway such as the TGFβ signaling pathway, and/or one or more small molecule agonists of a signal transduction pathway such as the canonical Wnt signaling pathway. The kit can also contain the ingredients for forming a 3D multilayered engineered skin construct to be provided with or incorporated into or onto a support structure (e.g., an artificial skin matrix) as described herein. In one embodiment, the kit includes one or more support structures for use with the skin compositions provided herein. A support structure can be a tissue engineering scaffold, matrix (e.g., artificial skin matrix), or material forming a matrix. The kit can also contain materials for transfecting the dermal fibroblasts to secrete a therapeutic protein of interest. In some embodiments, the dermal fibroblasts in the kit are genetically engineered to express the therapeutic protein of interest.

Unless defined otherwise, all technical and scientific terms used herein have the same meaning as commonly understood by one of ordinary skill in the art to which the invention belongs. Although any methods and materials similar to or equivalent to those described herein can be used in the practice or testing of the present invention, the preferred methods and materials are described herein.

As used herein, the phrase "consisting essentially of" means that the method or composition comprises the specified steps or ingredients and those that do not materially affect its basic characteristics.

As used herein, "about" means within 5% of a stated concentration range, density, temperature, or time frame.

The invention will be more fully understood upon consideration of the following non-limiting Examples. It is specifically contemplated that the methods disclosed are suited for pluripotent stem cells generally. Each mentioned publication is incorporated by reference as if set forth herein in its entirety.

EXAMPLES

Figures 2A, 2B, 2C, 2D, 2E, 2F, 2G, 2H, 2I:
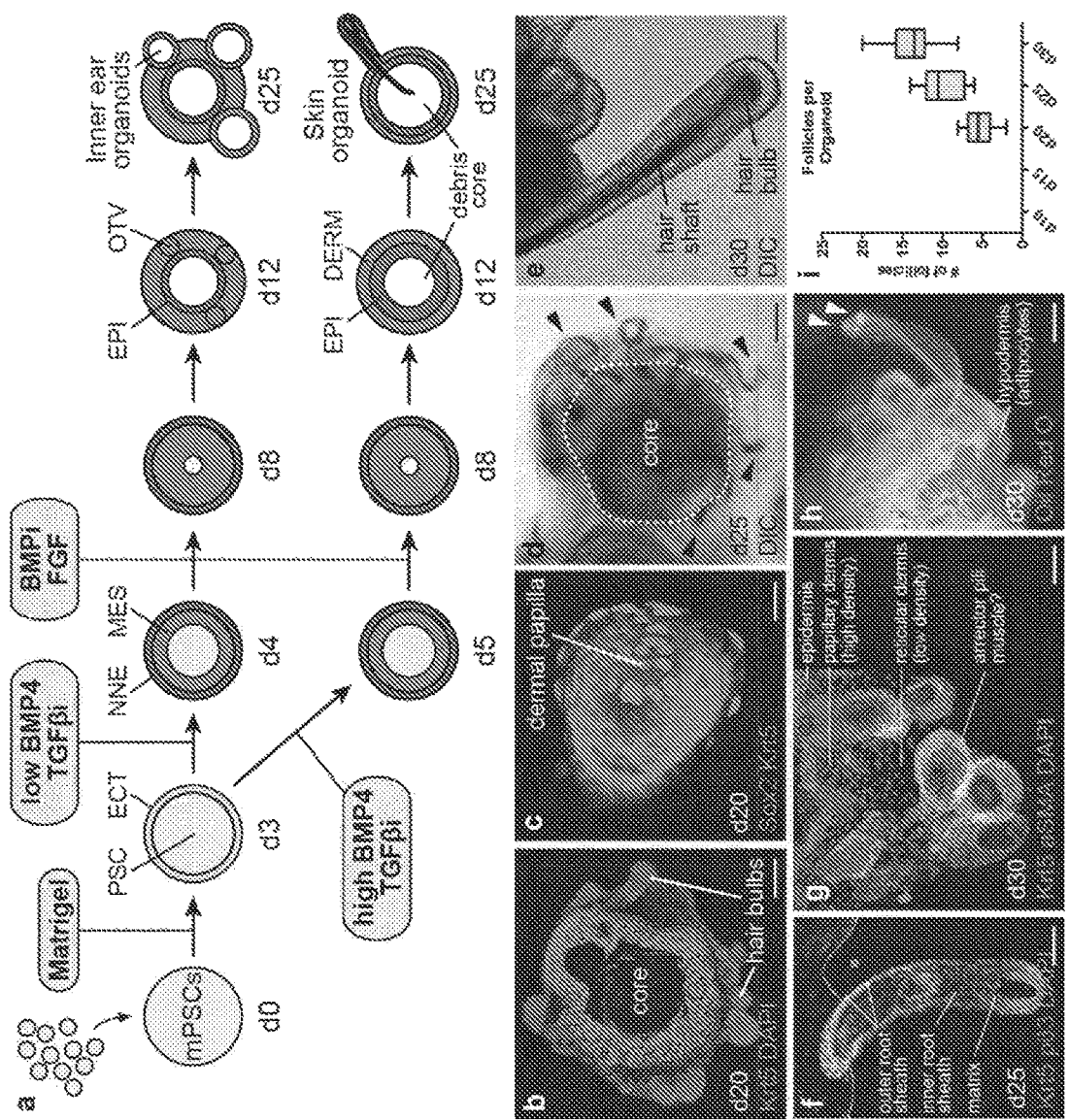
FIGS. 2A-2I describe skin organoids generated from mouse pluripotent stem cells (mPSCs). (A) Schematic of inner ear and skin organoid culture. (B) Cryosection of a skin organoid immunostained with anti-cytokeratin-5 (Krt5) and DAPI. (C) Sox2$^+$ dermal papilla cells in developing hair bulbs. (D) Cleared organoid with hair shafts extending into the organoid core (arrowheads). (E) Hair follicle protruding from a day 30 skin organoid. (F-H) Parts of hair follicle observed in skin organoids. (I) Quantification of hair follicles per aggregate over time in culture (error bars, min/max). ECT, ectoderm; MES, mesoderm; NNE, non-neural ectoderm; EPI, epidermis; OTP/OTV, otic placode/vesicle; DERM, dermis. Scale bars, 100 (B, D, H), 50 (E, F, G), 25 μm (C).
Figures 3A, 3B, 3C, 3D, 3E, 3F, 3G:
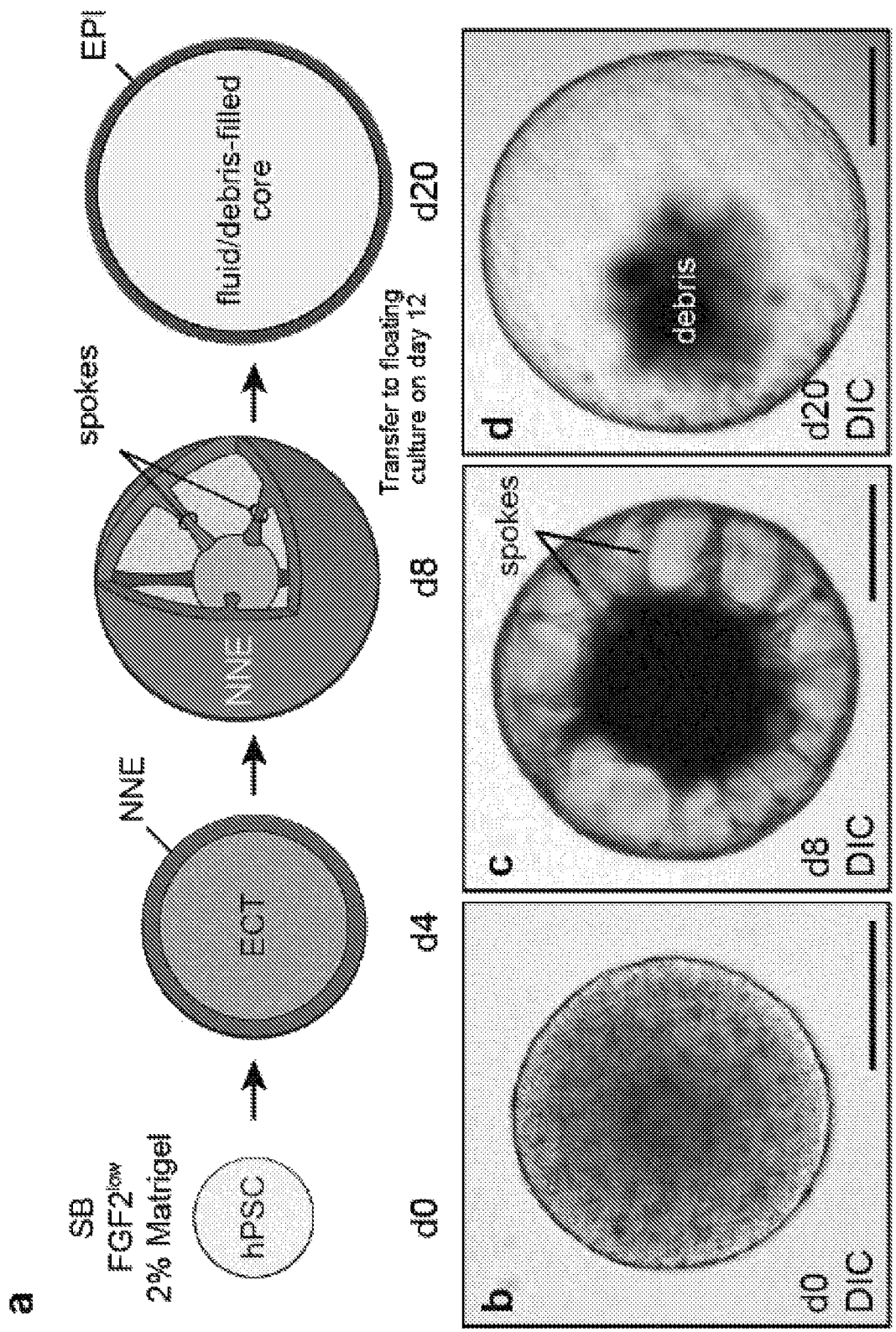
FIGS. 3A-3G demonstrate keratinocyte derivation from human pluripotent stem cell (hPSC) aggregates in three-dimensional (3D) culture. (A) Schematic of keratinocyte induction. (B-D) Differential interference contrast (DIC) microscopy images of aggregates on day 0, day 6, and day 20. Note the cellular structures containing cells migrating from the core to the epithelium. (E-F) Cryosection of day 3 aggregates showing non-neural TFAP2$^+$ cells in the outer epithelium and underlying tissues. (G) and (G') KRT5$^+$ TFAP2$^+$ keratinocyte-like cells in the epithelium of a day 20 aggregate. Scale bars, 200 (D), 100 (C, E, F), 50 μm (B).

Example 1—Protocol for Directed Differentiation of Mouse Pluripotent Stem Cells into Ectodermal and Mesodermal Germ Layers and Skin Organoids While investigating the induction of inner ear organoids, we noted the presence of epidermal keratinocytes. See Koehler, K. R., Mikosz, A. M., Molosh, A. I., Patel, D., & Hashino, E. (2013). Generation of inner ear sensory epithelia from pluripotent stem cells in 3D culture. *Nature*, 500 (7461), 217-221. To the day 3 culture was added bone morphogenetic protein-4 (BMP4) and a transforming growth factor beta (TGFβ) inhibitor, SB-431542 ("SB"), to promote non-neural induction in the epithelium. It was observed that the BMP4/SB treatment also induced a layer of mesodermal cells within the core of each aggregate (FIG. 2A). On day 4-5 the aggregates were treated with FGF-2 ("FGF") and a BMP inhibitor (LDN-193189; "LDN"). Surprisingly, after about 8-10 days of culture, the mesodermal cells migrated to the surface of the aggregates and formed a layer of tissue within which, under particular conditions, inner ear organoids can develop. We determined that increasing the concentration and duration of exposure to BMP4 could switch the aggregates' developmental trajectory from inner ear sensory tissue to skin (FIG. 2A). Moreover, some mouse pluripotent stem cell (mPSC) lines appeared to be predisposed to skin production. The resulting skin organoids contained an inner layer of epidermis and an outer layer of dermis tissue containing follicle-initiating dermal papilla cells (FIGS. 2B-C). By 25-30 days in culture, follicles produced ingrown hair shafts reflecting the inverted orientation of the tissue layers (FIGS. 2D-2E).

Many key features of postnatal follicles and dermis were represented in skin organoids, such as SOX2+ dermal papilla cells, aSMA+ arrector pili muscles, and Oil Red O+ hypodermal adipocytes (FIGS. 2F-2I). Importantly, the non-dermal cells, such as chondrocytes and neurons, which arise during inner ear organoid culture, were absent. Thus, the skin organoids comprised exclusively epidermis and dermis (n=42 skin organoids; 3 experiments). This protocol was repeated and yielded comparable results using multiple pluripotent stem cell lines (FIGS. 5A-5I). These data are believed to be the first to demonstrate generation of hair-producing skin from a pure population of pluripotent stem cells in vitro under defined conditions.

Example 2—In Vitro Production of Keratinocytes from Human Pluripotent Stem Cells We sought to develop a novel human non-neural induction protocol that could generate skin organoids. Human pluripotent stem cells of the WA25 cell line were dissociated in Essential 8 (E8) culture medium into single cells. Approximately 5000 cells were plated in each well of a 96-well V-bottom plate. Following 24 hours in culture, pluripotent cell aggregates that formed were transferred to 96-well U-bottom plates and cultured in a differentiation medium in the presence of Matrigel. This was considered "day 0" of differentiation (see FIG. 1).

In comparing our mouse pluripotent stem cell (mPSC) system with our human (hPSC) system, it was observed that hPSCs appear to produce different endogenous signaling molecules that must be added as exogenous factors for mPSC cultures. Assays were performed to identify key factors dictating non-neural ectoderm induction in hPSC aggregates. It was determined that treating hPSC aggregates with the TGF signaling inhibitor SB-431542 in a chemically-defined medium with or without a low concentration of BMP4 (<5 ng/ml) (CDM; Table 1) produces a surface epithelium of TFAP2$^+$ (AP2) non-neural ectoderm cells (FIGS. 3A-3F). After a 10-12 day incubation, the aggregates were transferred to a floating culture on low-cell attachment plates in organoid maturation medium (OMM; see Table 2). The non-neural induced aggregates ultimately generated a 3D spheroid comprising TFAP2$^+$KRT5$^+$ keratinocytes (FIGS. 3A, 3D, 3G), thus, producing the epidermal component of skin. This phenomenon was highly robust, occurring in 100% of WA25 hESC and mND2-0 hiPSC aggregates treated with SB or a combination of SB and BMP4 (n=40 aggregates per cell line across 4 experiments).

Figures 4A, 4B, 4C:
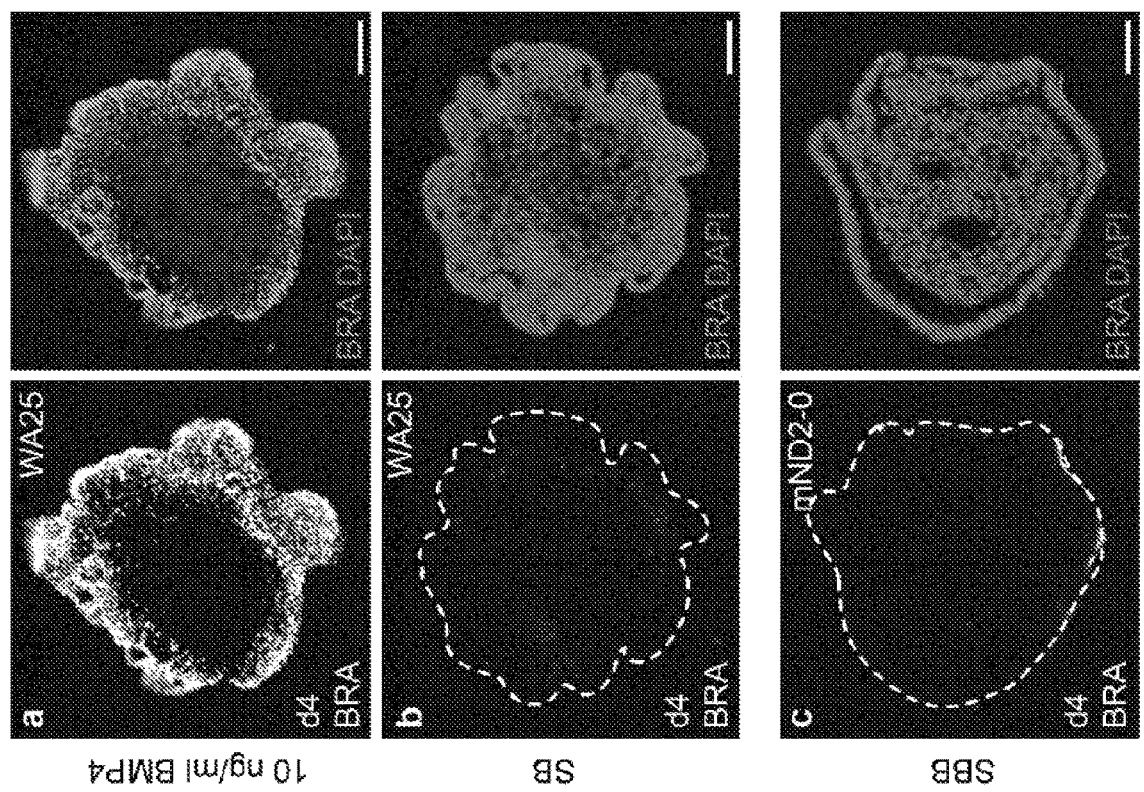
FIGS. 4A-4C demonstrate that non-neural ectoderm induction occurs without off-target induction of mesendodermal cells in human embryonic stem cells (WA25) and induced pluripotent stem cells (mND2-0). Representative Brachyury (BRA) immunohistochemistry in day 4 aggregates treated with 10 ng/ml BMP4 (a), 10 μM SB (b), and 10 μM SB+2.5 ng/ml BMP4 (c) on day 0. Scale bars, 50 μm.

We found that mesodermal cells (Brachyury+ cells) were not induced during the epidermal induction process, even when a low concentration of BMP-4 was used to induce non-neural ectoderm epithelium (FIGS. 4A-4C).

TABLE 1

Chemically-Defined Differentiation Medium (CDM)

| Component | Supplier | Cat. No. | Stock Concentration | Final Concentration | Volume (200 ml) |
|---|---|---|---|---|---|
| F-12 Nutrient Mixture | Gibco | 31765-035 | — | 49% (v/v) | 100 ml |
| IMDM | Gibco | 31980-030 | — | 49% (v/v) | 100 ml |
| CD Lipid Conc. | Invitrogen | 11905-031 | 100X | 1X | 2 ml |
| BSA | Sigma | A1470 | — | 5 mg/ml | 1 g |
| Insulin | Sigma | I9278 | 10 mg/ml | 7 ug/ml | 140 ul |

TABLE 1-continued

Chemically-Defined Differentiation Medium (CDM)

| Component | Supplier | Cat. No. | Stock Concentration | Final Concentration | Volume (200 ml) |
|---|---|---|---|---|---|
| Transferrin | Sigma | T8158 | 20 mg/ml | 15 ug/ml | 150 ul |
| Thioglycerol | Sigma | M6145 | 11.5 M | 450 uM | 8 ul |
| Normocin | Invitrogen | Ant-nr-1 | 50 mg/ml | 100 ug/ml | 400 ul | hPSC Culture:

Human PSCs (WA25 hESCs, passage 22-50; mND2-0 iPSCs, passage 28-46) were cultured in Essential 8 (E8) Medium or Essential 8 Flex Medium (E8f) (Invitrogen) supplemented with 100 μg/ml Normocin (Invivogen) on recombinant human Vitronectin-N (Invitrogen)-coated 6-well plates according to an established protocol[12,13]. At 80% confluency or every 4-5 days, the cells were passaged at a split ratio of 1:10-1:20 using an EDTA solution. Both cell lines were acquired from the WiCell Research Institute and arrived with a statement of verification and authenticity. Additional validation and testing information can be found on the cell line webpages, available at wicell.org/home/stem-cell-lines/catalog-of-stem-cell-lines/wa25.cmsx and wicell.org/home/stem-cell-lines/catalog-of-stem-cell-lines/mirjt7i-mnd2-0. cmsx on the World Wide Web. Cell lines were determined to be mycoplasma contamination-free using the MycoAlert Mycoplasma Detection Kit (Lonza).

hPSC Differentiation.

To start differentiation, hPSC cells were dissociated with StemPro Accutase (Invitrogen) and distributed, 5,000 cells per well, onto 96-well V-bottom plates in E8 medium containing 20 μM Y-27632 (Stemgent) and Normocin. Following a 48 hour incubation, the aggregates were transferred to 96-well U-bottom plates in 100 μl of Chemically Defined Medium (CDM) containing 4 ng ml$^{-1}$ FGF-2 (Peprotech), 10 μM SB-431542 (Stemgent), and, for some experiments, 2.5 ng ml$^{-1}$ BMP4 (Stemgent), and 2% Growth Factor Reduced (GFR) Matrigel (Corning) to initiate non-neural induction—i.e. differentiation day 0. CDM contained a 50:50 mixture of F-12 Nutrient Mixture with GlutaMAX (Gibco) and Iscove's Modified Dulbecco's Medium with GlutaMAX (IMDM; Gibco) additionally supplemented with 0.5% Bovine Serum Albumin (BSA), 1× Chemically Defined Lipid Concentrate (Invitrogen), 7 μg ml$^{-1}$ Insulin (Sigma), 15 μg ml$^{-1}$ Transferrin (Sigma), 450 μM Mono-Thioglycerol, and Normocin (see Table 1 for a detailed formulation). On differentiation day 12, the aggregates were pooled together and washed with freshly prepared Organoid Maturation Medium (OMM) containing a 50:50 mixture of Advanced DMEM:F12 (Gibco) and Neurobasal Medium (Gibco) supplemented with 0.5× N2 Supplement (Gibco), 0.5× B27 without Vitamin A (Gibco), 1× GlutaMAX (Gibco), 0.1 mM ß-Mercaptoethanol (Gibco), and Normocin (see Table 2 for a detailed formulation).

Choice of Media Components:

We used two media components that may lead to variability in results due to lack of definition or poor compatibility with human cells: GFR Matrigel and BSA. GFR Matrigel contains, <0.1 pg ml$^{-1}$FGF-2, <0.5 ng ml$^{-1}$ EGF, 5 ng ml$^{-1}$ IGF-1, <5 pg ml$^{-1}$ PDGF, <0.2 ng ml$^{-1}$ NGF, and 1.7 ng ml$^{-1}$ TGFβ. In particular, the TGFβ in GFR Matrigel may have impacted cell fate specification on day 12 or later because we did not include a TGFβ inhibitor in the media during that phase of culture. GFR Matrigel was chosen because it has been shown to be a reliable inducer of self-organizing epithelia from pluripotent stem cells in 3D culture[26]. A purified Laminin/Entactin complex (Corning) may be a suitable, fully chemically defined alternative[27]. In the CDM, BSA was chosen as a cost-effective and easy to dissolve alternative to Human Serum Albumin and Polyvinyl Alcohol (PVA), respectively. PVA has been shown to be a suitable chemically defined substitute for BSA in CDM[28]. Alternatively, an off-the-shelf GMP-grade medium, such as E6 Medium (Life Technologies) could be used in place of CDM.

TABLE 2

Organoid Maturation Medium (OMM)

| Component | Supplier | Cat. No. | Stock Concentration | Final Concentration | Volume (50 ml) |
| --- | --- | --- | --- | --- | --- |
| Adv DMEM/F12 | Gibco | 12491-015 | — | 49% (v/v) | 24.5 ml |
| Neurobasal | Gibco | 21103-049 | — | 49% (v/v) | 24.5 ml |
| N2 supplement | Gibco | 17502-048 | 100X | 0.5X | 250 µl |
| B27-Vitamin A | Gibco | 12587-010 | 50X | 0.5X | 500 µl |
| GlutaMAX | Gibco | 35050-079 | 100X | 1X | 500 µl |
| Mercaptoethanol | Gibco | 21985-015 | 55 mM | 0.1 mM | 91 µl |
| Normocin | Invitrogen | Ant-nr-1 | 50 mg/ml | 100 µl/ml | 100 µl |

The formulation set forth in Table 3 provides for 50 mL of medium, which should be used for <2 weeks. OMM is a custom-made hybrid of two media previously used to generate cerebral and gastric organoids[6,7]. B27 without Vitamin A was used to limit the influence of endogenously produced retinoic acid.

Figures 5A, 5B, 5C, 5D:
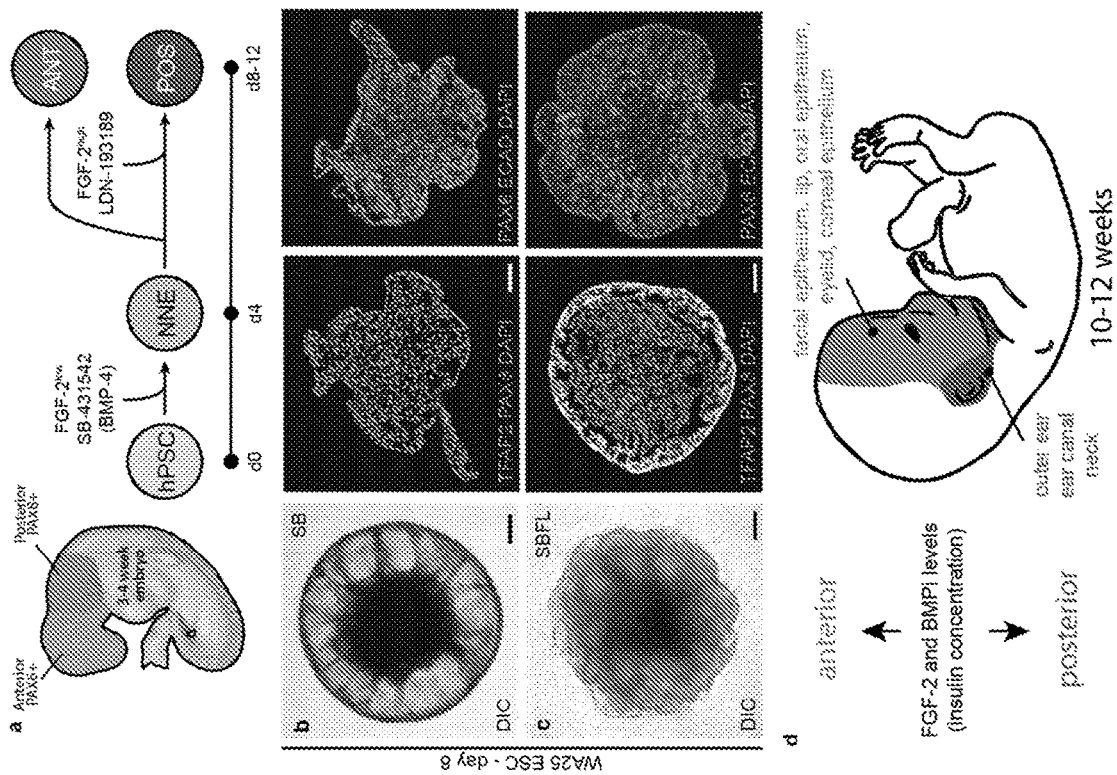
FIGS. 5A-5D demonstrate that treatment with FGF-2 and a BMP inhibitor (LDN) can generate posterior cranial surface ectoderm epithelium. A, Schematic of induction protocol. In the cranial region during embryonic development, the anterior surface ectoderm expresses the transcription factor PAX6, whereas the posterior surface epithelium expresses PAX8. Non-neural induced aggregates were treated with FGF-2 and LDN on day 4 and cultured for 8 to 12. Culture reagents in parentheses (i.e. BMP4) are optional depending on the cell line used. B, Aggregates treated with 10 μM SB-431542 and 4 ng/ml FGF-2 (denoted as SB) during days 0-12 generate TFAP2+ ECAD+ non-neural ectoderm epithelium that expresses the anterior marker PAX6, but not the posterior marker PAX8. C, Aggregates treated with 10 μM SB-431542 and 4 ng/ml FGF-2 (denoted as SB) during days 0-12 and 50 ng/ml FGF-2 and 200 nM LDN-193189 during days 4-12 generated TFAP2+ ECAD+ non-neural ectoderm epithelium that expressed the posterior marker PAX8, but not the anterior marker PAX6. D, schematic demonstrating the implications of these results for patterning aggregates along the anterior-posterior body axis. Tuning the FGF-2 and LDN concentrations could generate either anterior or posterior integumentary tissues.
Figures 6A, 6B, 6C, 6D:
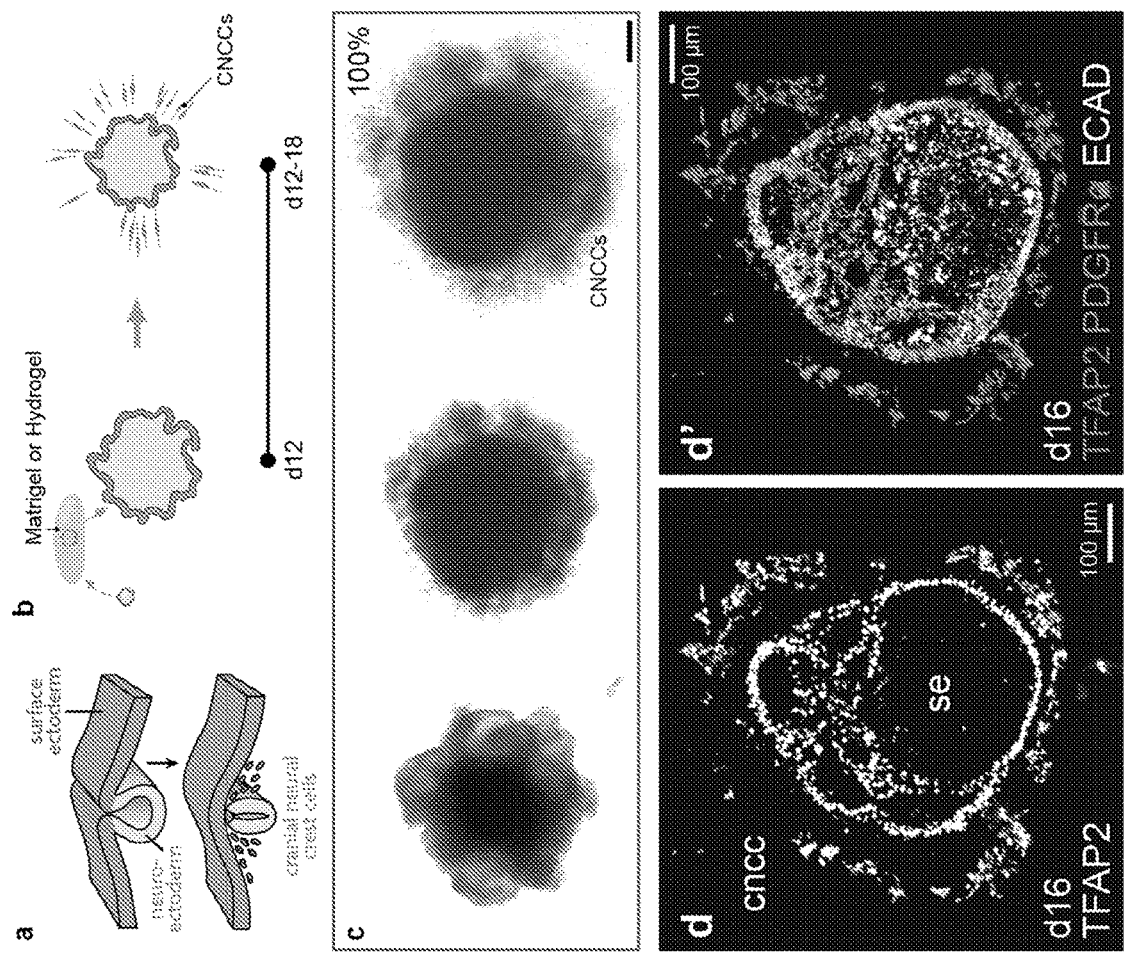
FIGS. 6A-6D' demonstrate that non-neural aggregates treated with SB/FGF/LDN during days 0-12 generate cranial neural crest cells (CNCCs) when embedded in Matrigel droplets. A, Schematic showing cranial neural crest cells. B, Schematic of transfer of day 12 aggregates to OMM in Matrigel® droplets. After treatment with SB on day 0 and FGF/LDN on day 4, day 12 aggregates were embedded in Matrigel droplets to support self-organization. C-D', without any additional treatment, the samples produced radially migrating TFAP2+ PDGFRa+, cranial neural crest cell-like cells (cncc). This phenomenon was observed in 100% of cell aggregates tested.

Example 3—In Vitro Production of Epidermal Keratinocytes and CNCC-Derived Dermal Fibroblasts Example 3 builds off of the epidermal induction method in Example 2. Cranial skin, unlike skin in other parts of the body, arises during development from interactions between the surface ectoderm and cranial neural crest cells (CNCCs). In our 3D culture of hPSCs, we carefully timed exposure of the cultured cells to small molecule and recombinant protein treatments in order to modulate the TGFß, BMP, FGF, and Wnt pathways and, thus, mimic the development of cranial surface ectoderm (FIGS. 3a-3f). To induce skin organoids, we treated non-neural induced aggregates (from Example 2) with FGF-2 and a BMP inhibitor on day 4 of differentiation (FIGS. 5A-5D). This treatment induced PAX8+ ECAD+ epithelium similar to that of the posterior cranial region of the developing head (FIG. 5C). Non-neural induced aggregates that were not treated had PAX6+ ECAD+ PAX8– epithelium indicative of anterior cranial surface epithelium (FIG. 5B). Thus, tuning FGF/LDN treatment concentration may be a sound strategy for generating surface epithelium of various tissue types along the cranial anterior/posterior axis (FIG. 5D).

As FGF/LDN treatment has been previously shown to generate tissue derivatives from the surface ectoderm/neural plate border (e.g., otic vesicles), we transferred day 12 aggregates to OMM in Matrigel® droplets. Remarkably, in this culture format, aggregates generated radially migrating cranial neural crest-like cells that expressed TFAP2 and PDGFRa (FIGS. 6A-6D'). The TFAP2+ ECAD+ epithelium remained centrally located in the aggregate (FIGS. 6A-6D').

Figures 7A, 7B, 7C:
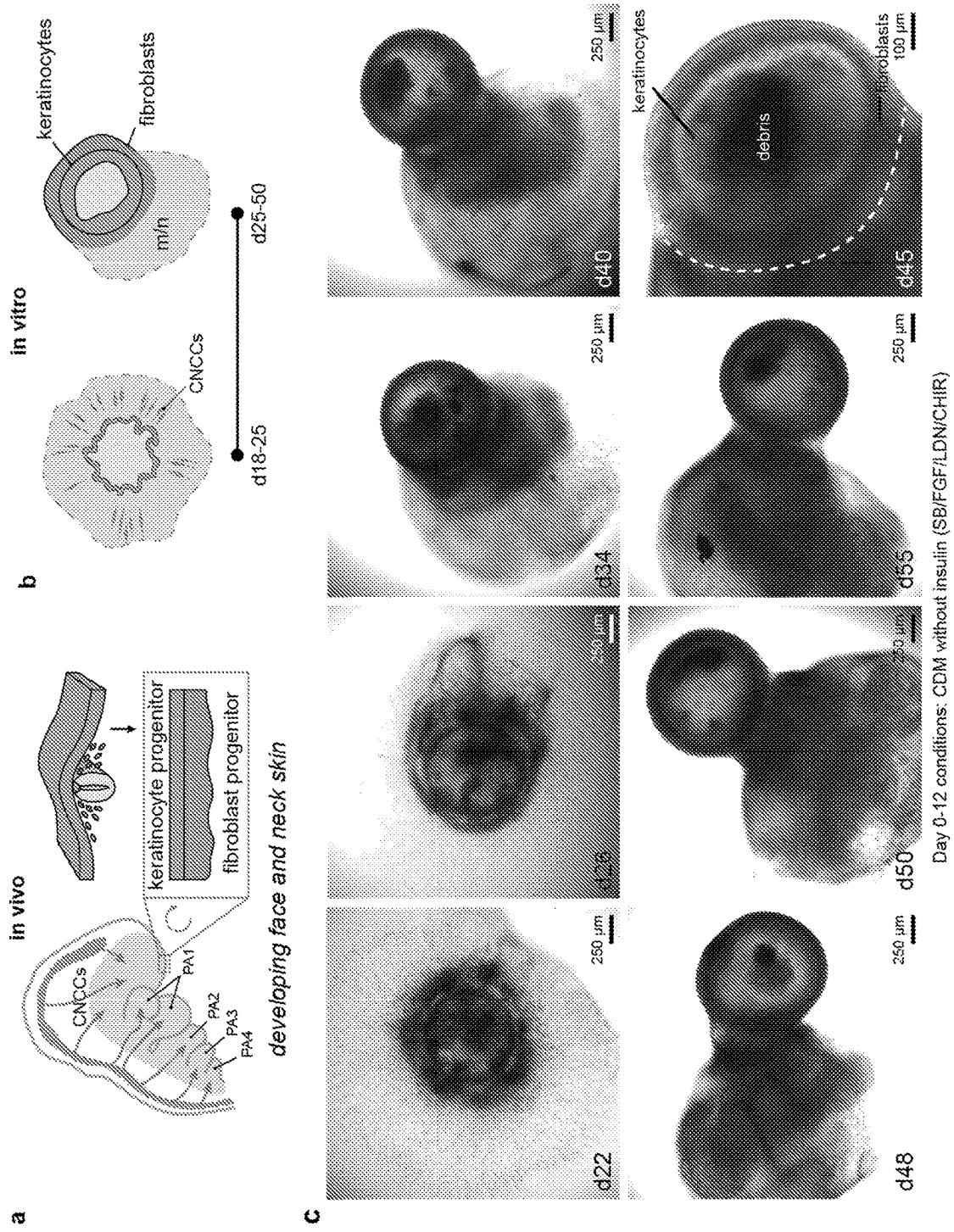
FIGS. 7A-7C demonstrate formation of skin organoids with an epidermal and dermal layer. A, overview of CNCC migration in the cranial region during development. A subset of post-migratory CNCC cells form dermal fibroblasts that abut the surface layer of keratinocyte progenitors. B, schematic of skin organoid formation during days 18-50 of differentiation. C, DIC images of skin organoid cysts forming. Note the inner layer of epidermis and cellular debris-filled core is covered by dermal tissue.
Figures 8A, 8B:
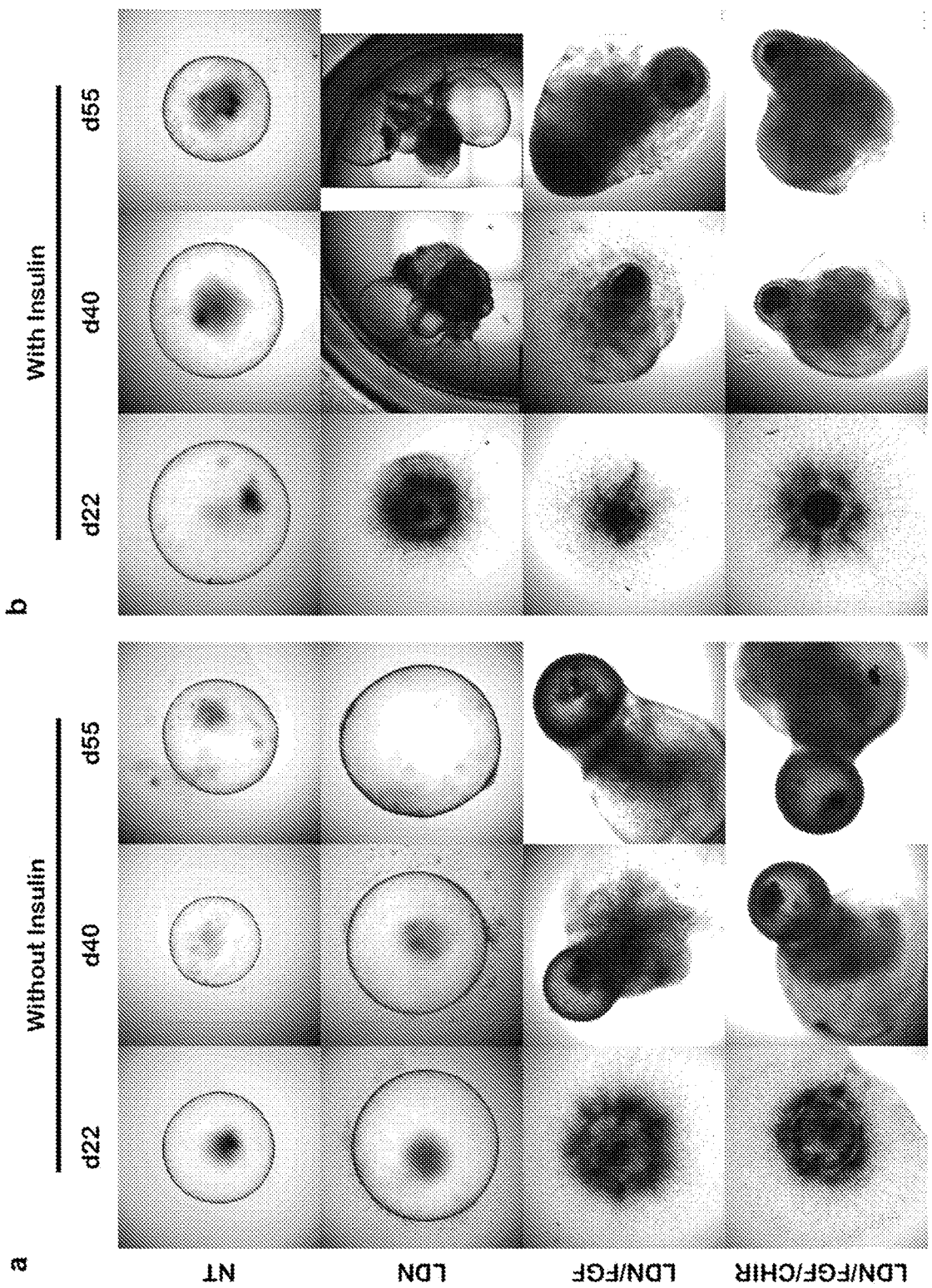
FIGS. 8A-8B demonstrate that removal of insulin from the differentiation medium generates larger skin organoids. A-b, Treatment conditions during days 0-12 were: no treatment (NT), LDN (from d4-d12), LDN/FGF (from d4-d12), and LDN/FGF (from d4-d12)+CHIR (from d8-d12). From days 22-55, skin organoids formed in LDN/FGF and LDN/FGF/CHIR conditions with or without insulin. However, skin organoids generated in insulin-free conditions had a long-axis diameter ~2.5-3.5 times greater than conditions with insulin (n=6 organoids/condition).
Figures 9A, 9B, 9C, 9D, 9E, 9F, 9G, 9H:
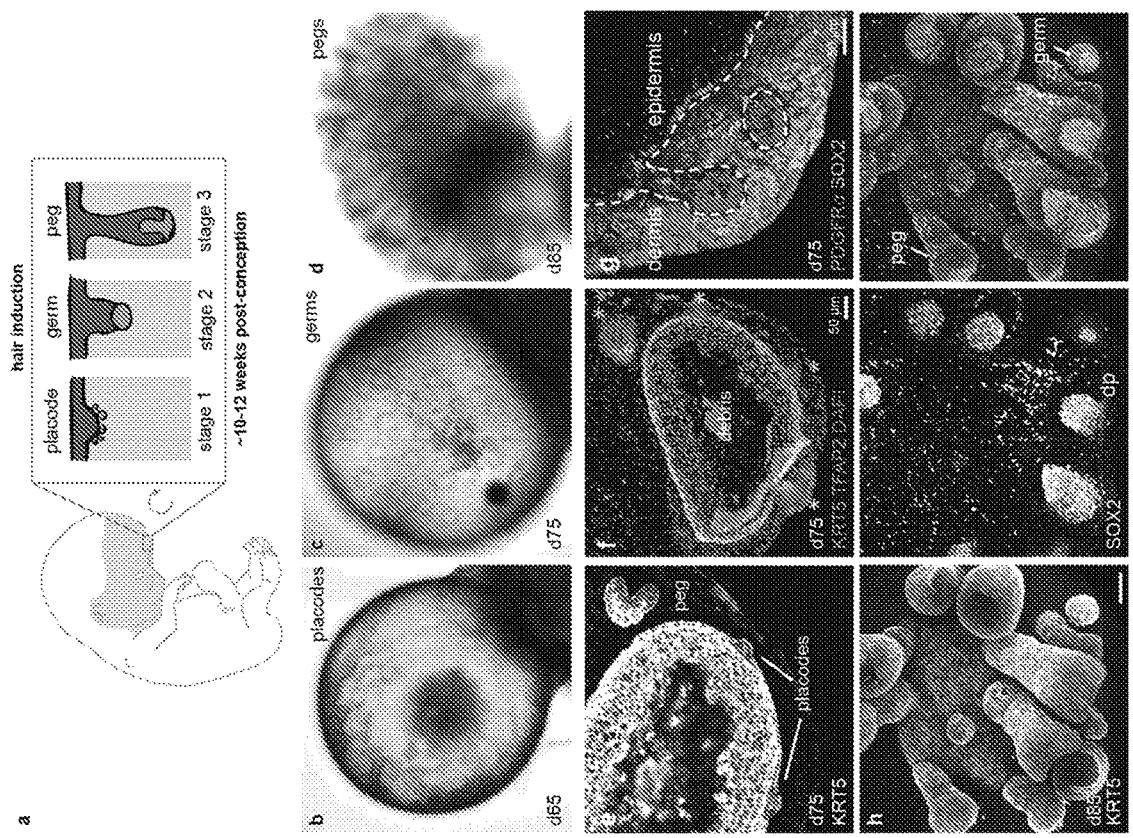
FIGS. 9A-9H demonstrate how hair follicles bud out from skin organoids and display characteristics of hair follicle development in vivo. A, schematic showing the first three stages of hair follicle induction in the human embryo. The process begins around 10-12 weeks (70-84 days) post-conception. B-D, DIC images of hair follicle placodes, germs, and pegs emerging from the epidermis of skin organoids between days 65-85—roughly equivalent to days 80-100 of human fetal development. E-G, The epidermis, comprising TFAP2+ KRT5+ keratinocytes coordinates with SOX2+ dermal papilla cells in the PDGFRa+ dermal layer to form hair follicle placodes, germs and pegs (asterisks in panel f). H, 3D reconstruction of day 85 skin organoids shows the formation of multiple hair follicles with clusters of SOX2+ dermal papilla cells.

We detached the droplet embedded aggregates from the plate and placed them in a rotating or shaking floating culture in OMM for up to 60 days. By 30-55 days of culture, skin organoids consisted of KRT5+ basal keratinocytes and PDGFRa+ dermal fibroblasts (FIGS. 7A-7C). The skin organoids developed as a cyst with an inner layer of epidermis and an outer layer of dermis. We next wondered what mechanism controlled the induction of skin organoids and tested various treatment plans with or without insulin in the CDM during days 0-12 of differentiation (FIGS. 8A-8B). After 12 days, the aggregates were transferred to Matrigel in OMM as previously mentioned. We found that the hair follicles were only generated by organoids that were induced by FGF/LDN treatment, regardless of insulin level (FIGS. 8A-8B). Aggregates that received no additional treatment (after the initial 10 µM SB+4 ng/ml FGF treatment) or LDN treatment alone, primarily formed keratinocyte cyts (FIGS. 8A-8B). Intriguingly, without insulin, the skin organoids were 2.5-3.5 times larger on average than insulin treated aggregates. We chose to continue our analysis with FGF/LDN and FGF/LDN/CHIR (without insulin) treated aggregates. Remarkably, stages of embryonic hair development were observed in skin organoids cultured longer than 60 days. Stages 1, 2, and 3 (placode, germ, and peg) of embryonic hair development occurred between days 60-85 (FIGS. 9A-9H; comparable results were observed in both conditions; FGF/LDN/CHIR conditions shown).

Figures 10A, 10B, 10C:
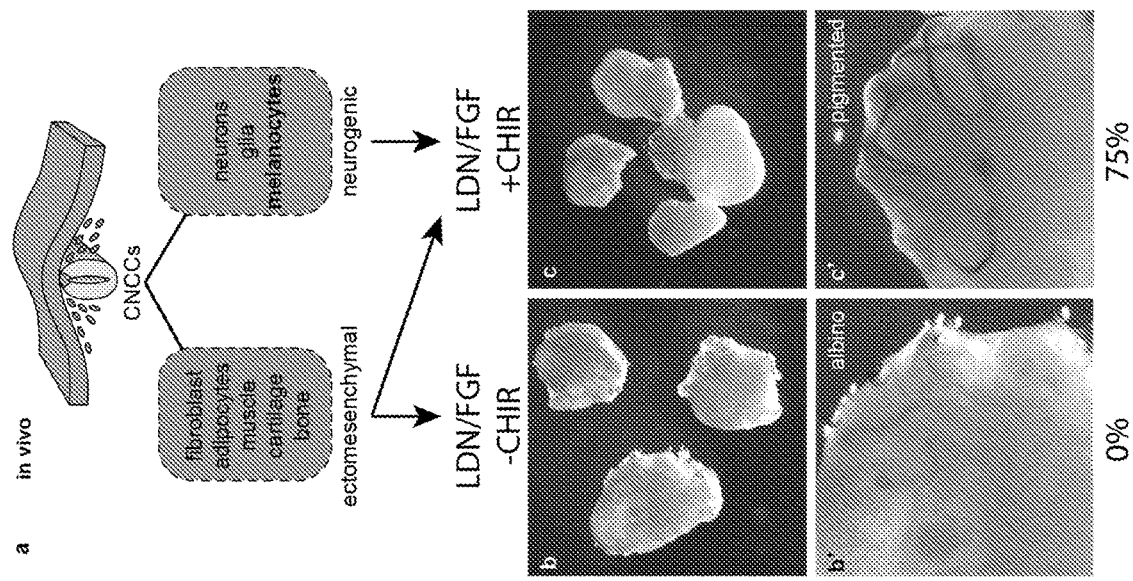
FIGS. 10A-10C' demonstrate that the composition of cells in the CNCC population of skin organoids can be controlled using CHIR treatment during days 8-12 of differentiation. A, Schematic showing that there are two populations of CNCCs: ectomesenchymal and neurogenic. Ectomesenchymal CNCCs generate fibroblasts, adipocytes, myocytes, cartilage, and bone, whereas neurogenic CNCCs produce neurons, glia, and melanocytes. B-C', Only organoids pretreated with CHIR99021, a Wnt signaling agonist, during days 8-12 produced pigmented hair follicles in 75% of organoids (10C, C'); thus, melanocytes were missing from non-CHIR treated samples (10B, B').
Figures 11A, 11B, 11C, 11D, 11E:
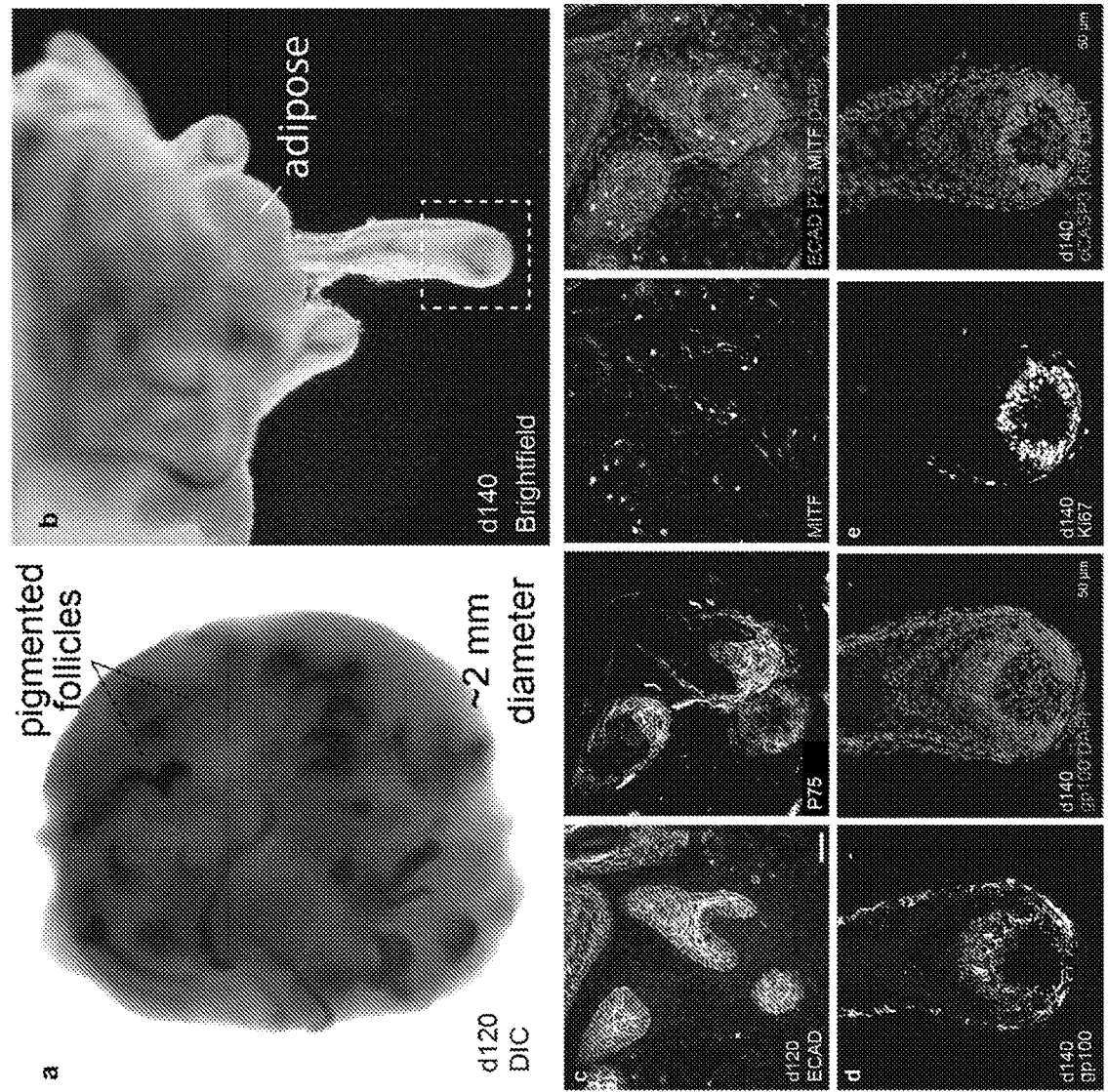
FIGS. 11A-11E demonstrate that skin organoids can produce pigmented skin and hair. A-B, Live cell images of day 120 and 140 skin organoids with pigmented follicles. C, MITF+ melanocytes were located in the E-Cadherin+ (ECAD+) follicular epidermis and in the dermis of day 120 organoids. P75 was expressed in the dermal papilla cells. D-E, Immunostaining of follicle highlighted by the box in panel B. D, Melanocytes in the hair follicle matrix region expressed gp100, denoting Melanin production. E, Ki67+ keratinocytes in the follicle bulb region and a lack of cleaved Caspase-3-expressing cells denotes that this organoid follicle is in the growth stage.

Overt pigmentation of the hair bulbs and shafts was observed between days 90-140 (FIGS. 10A-10C' and 11A-11B). We found that hair follicles derived from FGF/LDN aggregates were without pigment (FIGS. 10B, 10B') whereas follicles from FGF/LDN/CHIR aggregates were pigmented (10C, 10C'). Wnt activation is critical for neural crest induction in general; thus, it may play a role in specifically promoting melanogenic CNCCs (FIGS. 10A-10C). We confirmed that melanin-producing (gp100+ MITF+) melanocytes were present in the hair bulbs and epidermis (FIGS. 11A-11E).

We wondered if the entire pilosebaceous unit was present (FIG. 12A). At ~100 days in culture, we could detect sebaceous gland-like structures near the infundibulum of the organoid hair follicles (FIGS. 12B-12C). Immunostaining cryosectioned samples with LipidTOX (Life Technologies) confirmed that lipid-rich sebaceous gland cells were present (FIG. 12D). Starting around day 90, ITGA8+ aSMA+ arrector pili-like cells with elongated nuclei and large pearl-like adipocytes develop around the follicles, mimicking the development of the papillary/reticular and hypodermal dermis (FIGS. 12A-12G). KRT15+ hair follicle bulge stem cells were also present (FIGS. 12F and 12 G). As an indication of differentiation of basal keratinocytes, Filaggrin+ squames formed a stratum corneum-like layer in the skin organoid core layers (FIG. 12G). See Driskell et al., *Experimental Dermatology* 23, 629-631 (2014); Driskell et al., *Nature* 504, 277-281 (2013); and Driskell & Watt, *Trends in cell biology* (2014). doi:10.1016/j.tcb.2014.10.001.

Figures 13A, 13B, 13C, 13D:
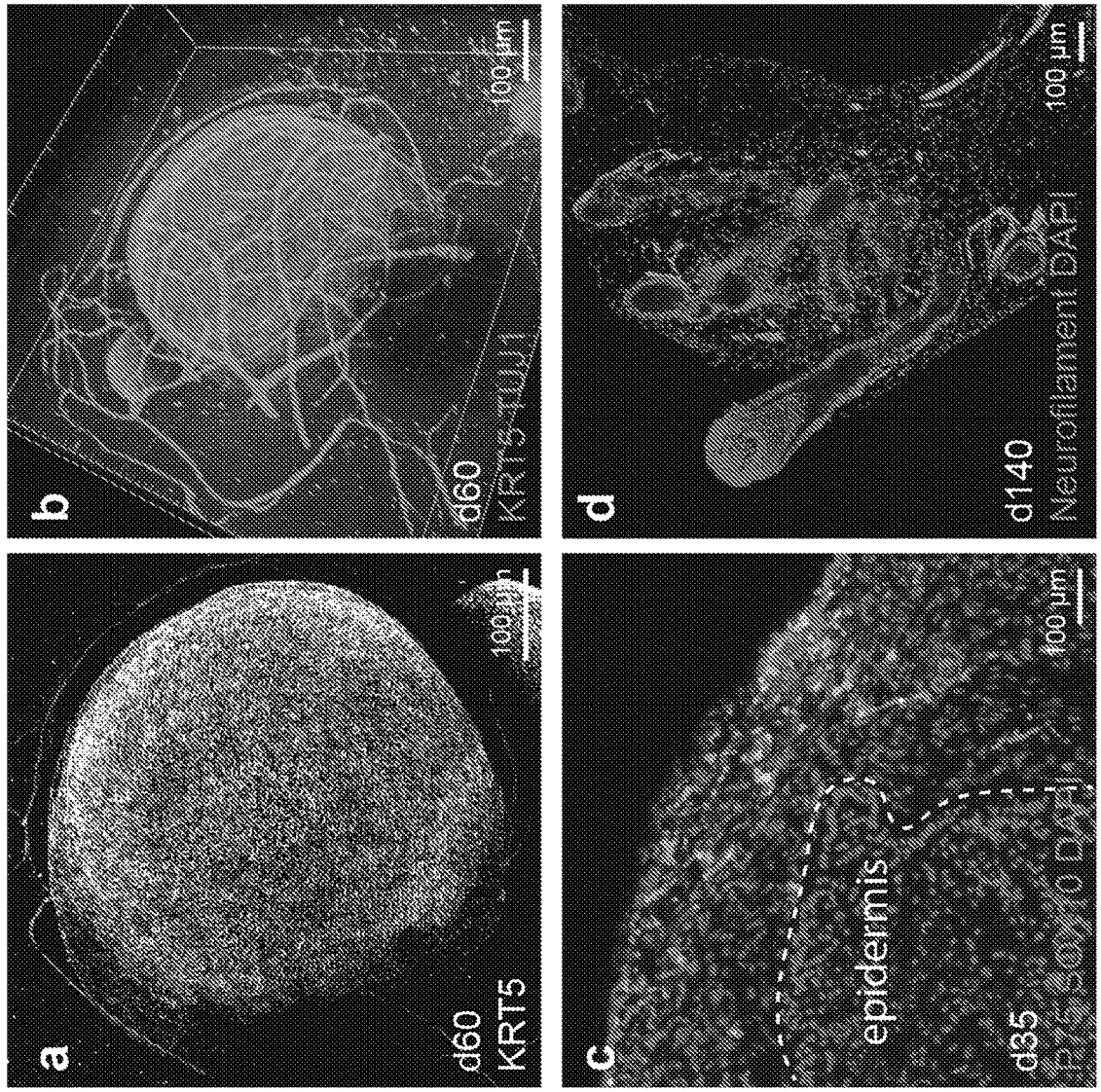
FIGS. 13A-13D demonstrate that CNCC-derived sensory neurons form a neural network in the dermis around skin organoids. A-B, A 3D reconstruction showing TUJ1+ neuronal processes wrapped around the KRT5+ epidermis of a day 60 skin organoid. C, By day 35 of differentiation, SOX10+ P75+ sensory neuron-like cells emerge in the CNCC-derived mesenchyme. D, In mature skin organoids (day 100-140), Neurofilament-H+ neuronal processes are interwoven around hair follicles and appear to make contact with the epidermal and follicular epithelia.

In addition to the essential pilosebaceous features mentioned above, we discovered that sensory neurons co-develop with skin organoids and forming intricate multi-axonal processes (fascicles), reminiscent of cranial sensory neurons (e.g. the facial nerve. Neuronal processes (Neurofilament-H/L+ TUJ1+) surrounded the epidermis of day 60 and day 140 skin orgnaoids (FIGS. 13A-13D). On day 35, we observed aggregations of SOX10+ P75+ CNCC-derived neural progenitor-like cells on the surface of the skin organoid dermal layer. These aggregated cells were reminiscent of cranial nerve ganglia that form during development. By day 140, The neuronal process appeared to contact the skin organoid epithelium and wrap around the circumference the follicles much like native human hair follicles (FIG. 13D).

Figures 14A, 14B, 14C, 14D, 14E, 14F, 14G:
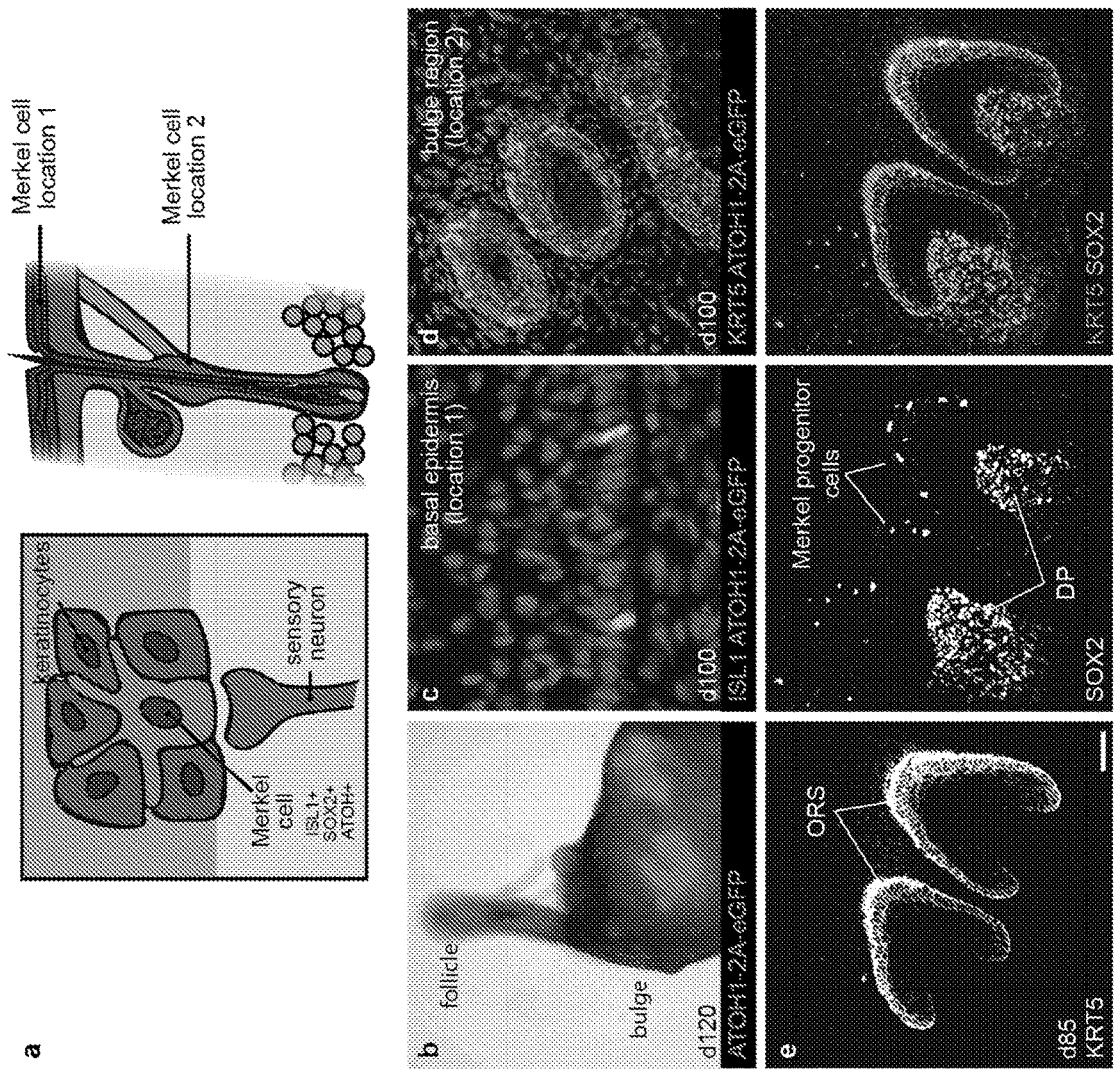
FIGS. 14A-14G demonstrate that skin organoid epidermis produces Merkel cells that receive innervation from neighboring sensory neurons. A, Schematic describing the orientation and placement of Merkel cells within the epidermis and follicle. B, Exemplary data from skin organoids generated with an ATOH1-2A-eGFP stem cell line showing Merkel cell progenitor-like cells (eGFP+) in the bulge region of a hair follicle. C-E, The eGFP+ cells are distributed in the basal epidermis and follicular outer root sheath like native Merkel progenitor cells. The eGFP+ cells are also Islet1+ (ISL1+) consistent with Merkel cell development. F-G, Co-labeling of day 140 orgnaoids with ISL1 and Neurofilament-L (NF-L) reveals that Merkel cells receive innervation from sensory neurons in the organoid dermal layer.

Epidermal-derived mechanosensory cells called Merkel cells are a primary target of sensory neurons in the skin (FIG. 14A). We examined skin organoids for the presence of Merkel cells using a combination of IHC and live cell imaging using a novel ATOH1-2A-eGFP reporter hESC line (WA25 genetic background; developed in collaboration with Drs. Eri Hashino and Jing Nie). The transcription factor ATOH1 is highly expressed in Merkel progenitor cells during development. See Narisawa, Y., Hashimoto, K., & Kohda, H. (1994). Merkel Cells of the Terminal Hair Follicle of the Adult Human Scalp. *Journal of Investigative Dermatology*, 102(4), 506-510 and Wright, M. C., Reed-Geaghan, E. G., Bolock, A. M., Fujiyama, T., Hoshino, M., & Maricich, S. M. (2015). Unipotent, Atoh1+ progenitors maintain the Merkel cell population in embryonic and adult mice. *The Journal of Cell Biology*, 208(3), 367-379. We found that ATOH1-2eGFP+ cells were evenly distributed throughout the epidermis and concentrated in the bulge region of developing follicles (FIGS. 14B-14D). The ATOH1-2A-eGPF$^+$ Merkel-like cells were also Islet1$^+$ SOX2$^+$ (FIGS. 14C-14G). Remarkably, co-immunostaining for ISL1 (Merkel cells) and Neurofilament-L (Merkel cells and sensory neurons) revealed that sensory neurons extend processes into the epidermis and appear to make synaptic contacts with Merkel cells by day 140 of differentiation (FIGS. 14F-14G).

To our knowledge, this organoid system produced the most comprehensive array of cutaneous cell types of any PSC-based model that has been described. Using a human embryonic stem cell line (WA25, WiCell Institute), we replicated these findings in seven separate experiments with a success rate of 96.4% (27/28) of organoids producing HFs, suggesting that the method is highly reproducible. Recently, we confirmed that the method works in an hiPSC line (mND2-0, WiCell Institute) with similar efficiency (91.7%, 11/12). The average number of follicles per organoids varied, with 22±11 follicles for hESCs and 14±9 follicles for hiPSCs.

Modifications to Differentiation Approach Described in Example 2:

After 4 days of incubation, 25 µl of CDM containing a 250 ng ml$^{-1}$ FGF-2 (50 ng/ml final concentration) and 1 µM LDN-193189 (200 nM final concentration) was added to the pre-existing 100 µl of media in each well. After an additional 4 days (8 days total), 250 of CDM was added to the media. For some experiments, CDM containing 18 µM CHIR99021 (3 µM final concentration; Stemgent) was added to the pre-existing 125 µl of media in each well. During day 12 transfer to OMM, aggregates were resuspended in ice cold undiluted GFR Matrigel and placed in approximately 25 µl droplets on the surface of a 100 mm bacterial culture plate. After at least 30 minutes of incubation at 37° C., the droplets were bathed in 10 ml of OMM. To avoid Matrigel droplet induction, the aggregates can be washed and plated individually into each well of a 24-well low cell adhesion plate in OMM containing 1% GFR Matrigel. After 18 days of differentiation, the CHIR was removed from the medium by washing and the droplet aggregates were moved to a floating culture. Droplets were carefully dislodged using a wide-mouth 1000P tip and transferred to 75 ml of fresh OMM in a 125 ml disposable spinner flask (Corning). Spinner flasks were maintained on an in-incubator stir plate (Thermo Scientific) at 65 RPM for up to 180 days of differentiation. For some experiments, the aggregates were maintained in individual wells of 24-well low-cell adhesion plates in 1 ml of OMM on an in-incubator orbital shaker (Thermo Scientific) for up to 140 days.

Example 4—Dissociated Mouse Skin Organoids Re-Organize into Epidermal and Dermal Layers in Air-Liquid Interface 3D Cultures To test whether skin organoids could be reconfigured into a bilayer, we dissociated mouse skin organoids prior to hair follicle development and plated the organoid cells in an air-liquid interface culture. Importantly, we did not separate the epidermal and dermal populations as is typically necessary. Timing of dissociation is likely critical, since the ability of organoid cells to self-organize should diminish over time. We chose to dissociate day 9 skin organoids, just after the onset of KRT5 expression in the epidermis. Briefly, 45 organoids (per condition) at day 9 were fully dissociated into single cells, using AccuMax (EMD Millipore, Darmstadt, Germany). The dissociated cells were plated on top of a Matrigel layer in a transwell porous membrane culture insert (MilliCell, PTFE, 0.4 µm pore; condition 1) or directly on a transwell membrane as a droplet of cells and Matrigel mixture (condition 2), and cultured in the presence of organoid medium containing ROCK inhibitor (FIGS. 15A-B). On day 12, spent medium was replenished, and the medium inside the transwell was removed to provide the air-liquid interface culture environment, expecting cells to rearrange and organize into different layers of skin. By day 23, about 1 mm thick cell layers were formed both in conditions 1 and 2, and were fixed and processed for immunohistochemistry. The layer formed in condition 1 was composed of a KRT5$^+$ keratinocyte layer and a PDGFRa$^+$ (CD140a$^+$) fibroblast layer, side by side. The layer formed in condition 2 was full of KRT5$^+$ keratinocyte cysts with PDGFRa$^+$ fibroblasts. Importantly, the organoid cells survived and were able to self-organize under these conditions. Taken together, this method—fully dissociating organoids at day 9 and re-plating dissociated cells in a layer—shows a potential of generating full-thickness skin with different layers and, possibly, appendages of skin.

Figure 16:
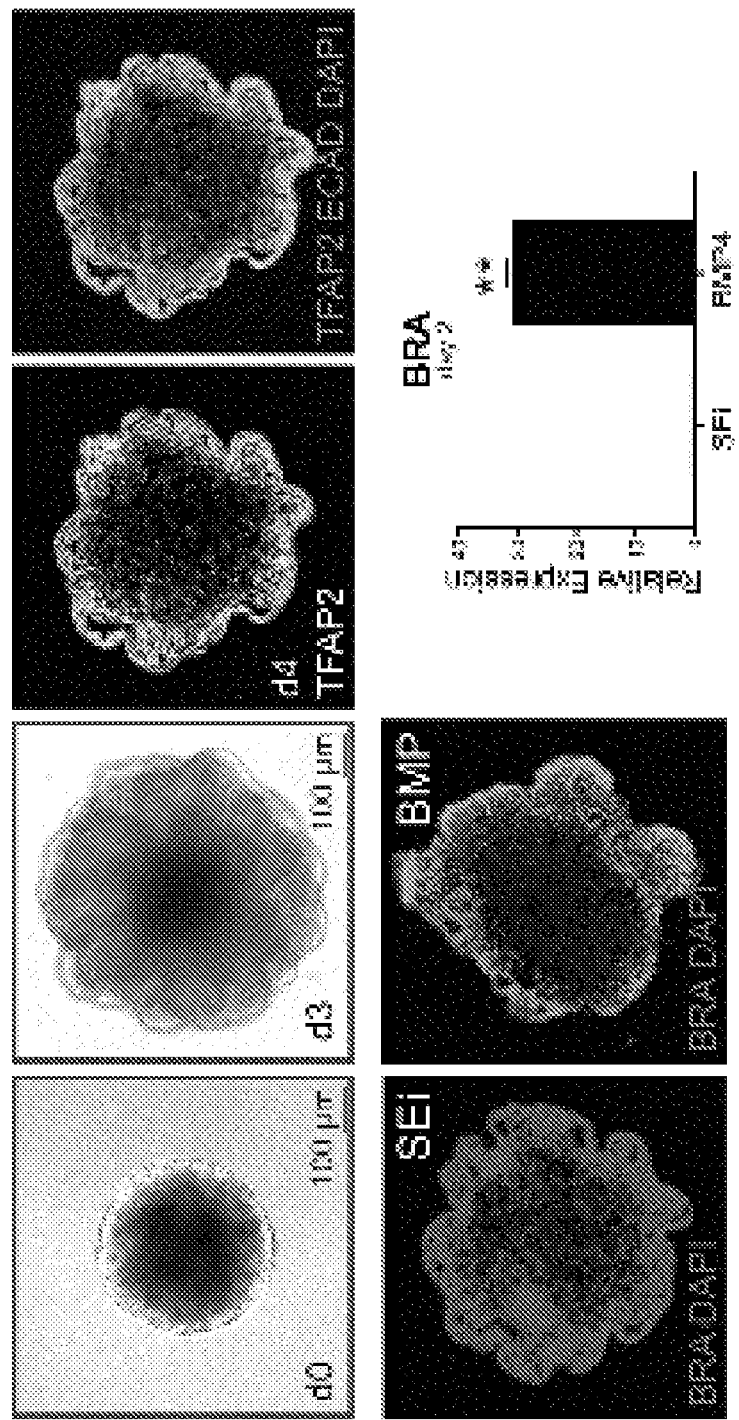
FIG. 16 demonstrates that surface ectoderm induction (SEI) in hPSC-derived aggregates occurs without mesoderm induction. With human PSCs, TGFβ inhibition and endogenous BMP signaling promotes formation of TFAP2+ ECAD+ surface ectoderm by 3-6 days of differentiation. These aggregates lacked mesoderm, whereas mesoderm is induced (BRA+) cells in the aggregates by BMP treatment alone.
Figure 17:
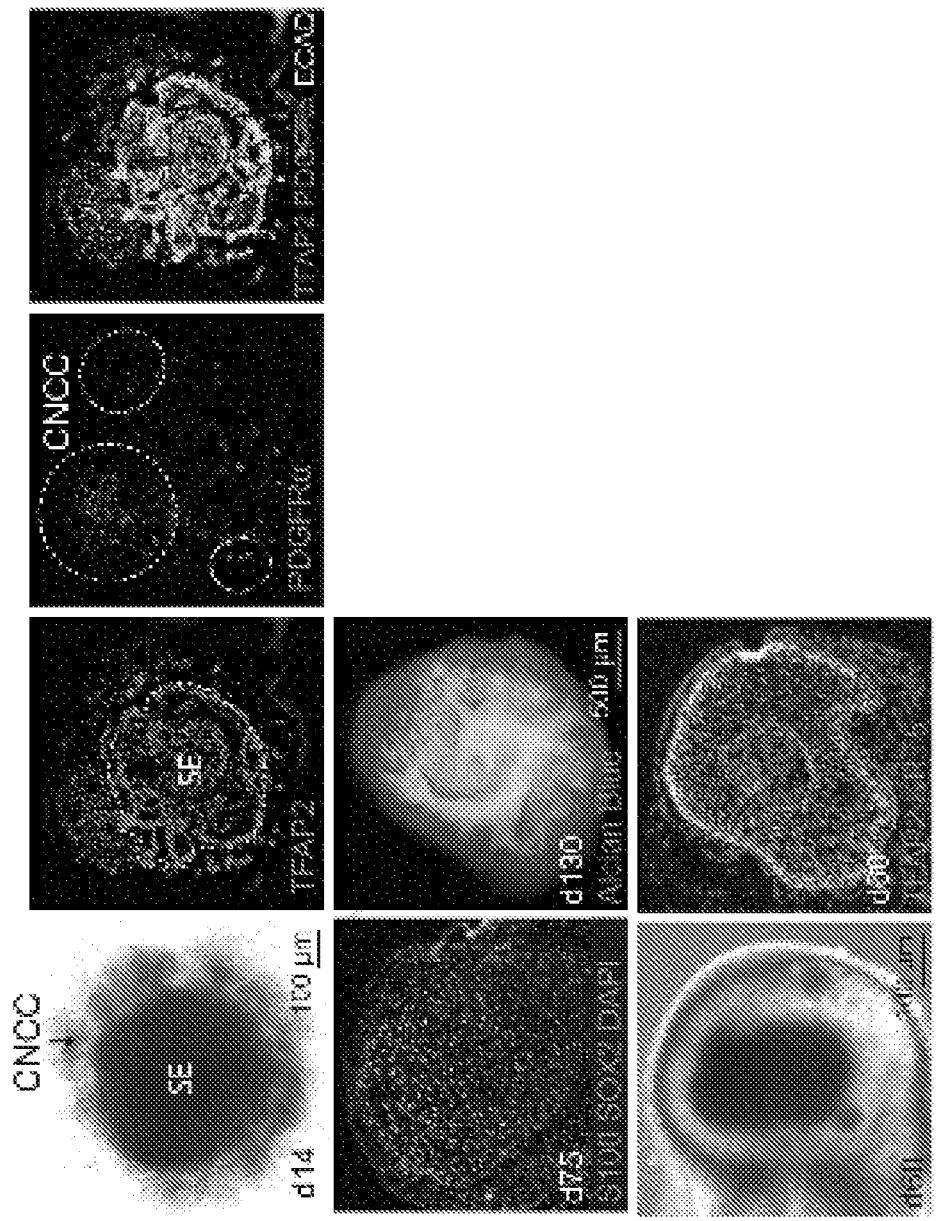
FIG. 17 demonstrates that time treatment of FGF and inhibition of BMP promotes co-induction of CNCCs with surface ectoderm. Inhibition of BMP signaling together with FGF treatment co-induces TFAP2+ and PDGFRa+ CNCCs with TFAP2+ and ECAD+ surface ectoderm. Ultimately, such co-induction induced CNCC-derived tissue types including cartilage and skin organoids.

Example 5—Recapitulating Craniofacial Developing in Pluripotent Stem Cell-Derived Organoids Craniofacial development is fundamental to survival and social communication; however, millions of individuals suffer from improperly developed or surgically reconstructed facial features due to genetic mutations, removal of cancerous tumors, or severe burns. To better define facial development and identify novel cell therapies for facial defects, we will benefit from in vitro systems that model the mechanism by which the craniofacial complex arises in the embryo. The human face and mouth forms from an intermingling of ectoderm, endoderm, mesoderm, and cranial neural crest cells (CNCCs). Specifically, we are interested in mechanisms dictating CNCC self-organization into facial features, such as the facial dermis and cartilage. We developed a three-dimensional (3D) culture system using pluripotent stem cells (PSCs) to obtain inner ear organoids as well as a diverse group of mesenchymal tissues, such as cartilage, skin, and muscle. Here, we show that two critical components of the craniofacial complex, the surface ectoderm and CNCCs, can be co-induced from human PSCs (hPSCs) in 3D culture. We used small molecules and recombinant proteins to control BMP, TGF-β, and FGF signaling in differentiating hPSC aggregates. As shown in FIG. 16, TGFβ inhibition and endogenous BMP signaling promotes formation of TFAP2+ ECAD+ surface ectoderm by 3-6 days of differentiation. These aggregates lacked mesoderm, whereas mesoderm is induced (BRA+) cells in the aggregates by BMP treatment alone. As shown in FIG. 17, time treatment of FGF and inhibition of BMP promoted co-induction of CNCCs with surface ectoderm. Inhibition of BMP signaling together with FGF treatment co-induces TFAP2+ and PDGFRa+ CNCCs with TFAP2+ and ECAD+ surface ectoderm. Ultimately, such co-induction induced CNCC-derived tissue types including cartilage and skin organoids.

After two weeks of guided differentiation, organoids emerged containing an inner layer of KRT5$^+$ surface epithelium and an outer layer of AP2$^+$ PDGFRα$^+$ CNCC-like cells, reminiscent of the cranial ectomesenchyme. Remarkably, these tissues self-organize into stratified epidermis and dermis, as well as cartilaginous masses, mimicking embryonic cranial development. Thus, our human PSC-based in vitro system offers an opportunity for in-depth investigation of the mechanisms underlying craniofacial development, modeling neurocristopathies, and identifying novel regenerative therapies.

We claim:

1. A method of obtaining a three-dimensional multilayered human skin composition, the method comprising:
    (a) culturing human pluripotent stem cell aggregates in a chemically defined culture medium comprising FGF-2 and an inhibitor of Transforming Growth Factor Beta (TGFβ) mediated signaling for about 4 days, whereby non-neural epithelium forms within the aggregates;
    (b) treating the stem cell aggregates of (a) with FGF-2 and an inhibitor of Bone Morphogenetic Protein (BMP) for about 4 to about 8 days;
    (c) embedding the cultured aggregates of (b) in a porous substrate comprising extracellular matrix components; and
    (d) culturing the embedded aggregates of (c) in floating culture for at least 48 days under conditions that promote self-assembly of cells within the embedded aggregates into a three-dimensional, multilayered human skin composition comprising an epidermal layer, a dermal layer, and a plurality of cells capable of forming a functional hair follicle.

2. The method of claim 1, wherein the porous substrate comprises a semi-solid culture medium.

3. The method of claim 1, wherein the porous substrate is a three-dimensional (3D) porous biomaterial.

4. The method of claim 3, wherein the three-dimensional (3D) porous biomaterial is a chemically defined hydrogel.

5. The method of claim 1, wherein the inhibitor of TGFβ-mediated signaling is selected from the group consisting of SB431542 and A-83-01.

6. The method of claim 1, wherein the extracellular matrix components are a basement membrane extract (BME).

7. The method of claim 1, wherein the epidermal layer is in direct contact with the dermal layer.

8. The method of claim 1, wherein the epidermal layer comprises P63$^{+KRT}$5$^+$epidermal keratinocytes.

9. The method of claim 1, wherein the dermal layer comprises follicle-initiating dertnal papilla cells.

10. The method of claim 1, wherein the plurality of cells capable of forming a functional hair t Niche comprises cells selected from the group consisting of mesenchymal stem cells, dermal papilla cells, dermal sheath cells, and follicular epidermal stem cells.

11. The method of claim 1, further comprising seeding the porous substrate in (c) with one or more cell types selected from the group consisting of epidermal immune cells, mesoderm-derived cells, and endothelial cells.

12. The method of claim 11, wherein the epidermal immune cells are Langerhan's cells.

13. The method of claim 1, wherein the inhibitor of BMP is LDN-193189.

14. The method of claim 1, wherein the inhibitor of TGFβ-mediated signaling is selected from the group consisting of SB431542 and A-83-01, and wherein the inhibitor of BMP is LDN-193189.

15. The method of claim 1, wherein the inhibitor of TGFl3-mediated signaling is SB431542, and wherein the inhibitor of BMP is LDN-193189.

* * * * *

UNITED STATES PATENT AND TRADEMARK OFFICE
CERTIFICATE OF CORRECTION

PATENT NO. : 11,021,688 B2
APPLICATION NO. : 15/769139
DATED : June 1, 2021
INVENTOR(S) : Karl R. Koehler et al.

Page 1 of 1

It is certified that error appears in the above-identified patent and that said Letters Patent is hereby corrected as shown below:

In the Specification

Column 8, Line 46, "ALKS" should be --ALK5--.

Column 20, Line 63, "ml⁻ FGF-2" should be --$ml^{-1}$ FGF-2--.

In the Claims

Column 26, Claim 8, Line 18, "$P63^{+KRT}5^{+}$" should be --$P63^{+}KET5^{+}$--.

Column 26, Claim 9, Line 20, "dertnal" should be --dermal--.

Column 26, Claim 10, Line 22, "t Niche" should be --follicle--.

Signed and Sealed this
Third Day of August, 2021

Drew Hirshfeld
*Performing the Functions and Duties of the
Under Secretary of Commerce for Intellectual Property and
Director of the United States Patent and Trademark Office*